(12) United States Patent
Bodie et al.

(10) Patent No.: US 9,868,958 B2
(45) Date of Patent: *Jan. 16, 2018

(54) FILAMENTOUS FUNGI HAVING AN ALTERED VISCOSITY PHENOTYPE

(75) Inventors: Elizabeth A. Bodie, San Carlos, CA (US); Robert James Pratt, II, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/113,549

(22) PCT Filed: Apr. 20, 2012

(86) PCT No.: PCT/US2012/034405
§ 371 (c)(1),
(2), (4) Date: Dec. 19, 2013

(87) PCT Pub. No.: WO2012/145596
PCT Pub. Date: Oct. 26, 2012

(65) Prior Publication Data
US 2014/0127817 A1 May 8, 2014

Related U.S. Application Data

(60) Provisional application No. 61/478,162, filed on Apr. 22, 2011, provisional application No. 61/478,160, filed on Apr. 22, 2011, provisional application No. 61/480,602, filed on Apr. 29, 2011, provisional application No. 61/480,629, filed on Apr. 29, 2011, provisional application No. 61/480,610, filed on Apr. 29, 2011.

(51) Int. Cl.
| | |
|---|---|
| *A61K 39/00* | (2006.01) |
| *C07H 21/02* | (2006.01) |
| *C07H 21/04* | (2006.01) |
| *C12N 15/79* | (2006.01) |
| *C12N 1/14* | (2006.01) |
| *C12N 15/80* | (2006.01) |
| *C12N 1/36* | (2006.01) |
| *C12N 9/24* | (2006.01) |

(52) U.S. Cl.
CPC .............. *C12N 15/79* (2013.01); *C12N 1/14* (2013.01); *C12N 1/36* (2013.01); *C12N 9/2405* (2013.01); *C12N 15/80* (2013.01)

(58) Field of Classification Search
CPC .... A61K 39/00; A61K 39/0002; C07K 14/37; C12N 1/14; C12R 1/645
USPC .............. 424/274.1; 536/23.1, 23.7
See application file for complete search history.

(56) References Cited

U.S. PATENT DOCUMENTS

| | | | |
|---|---|---|---|
| 7,279,564 B2 * | 10/2007 | De Nobel et al. | ............ 536/23.1 |
| 9,593,341 B2 * | 3/2017 | Bodie | ...................... C12N 1/14 |
| 2004/0224388 A1 | 11/2004 | Dunn-Coleman | |

FOREIGN PATENT DOCUMENTS

| | | |
|---|---|---|
| WO | WO 2001/09352 | 2/2001 |
| WO | WO 2002/079399 | 2/2001 |
| WO | WO 2005/001036 | 1/2005 |
| WO | WO 2012/027580 | 3/2012 |

OTHER PUBLICATIONS

Schumacher, J. et al. Eukaryotic Cell, vol. 7, No. 4, pp. 584-601, Apr. 2008.*
Altschul et al., "Basic local alignment search tool," ( J. Mol. Biol. 215:403-10)(1990).
Altschul et al., "Local Alignment Statistics," Meth. Enzymol. 266:460-80) (1993).
Borgia, et al., "The *Orla* gene from Aspergillus nidulans encodes a trehalose-6-phosphate phosphatase necessary for normal growth and chitin synthesis at elevated temperatures," Molecular Microbiology, vol. 20, No. 6, pp. 1287-1296, 1996.
Choi, J. et al., MoCRZ1, a gene encoding a calcineurin-responsive transcription factor, regulates fungal growth and pathogenicity of Magnaporthe oryzae, Fungal Genetics and Biology, 46:3, 243-254 (2009).
Cramer, R. et al., "Calcineurin target CrzA regulates conidial germination, hyphal growth, and pathogenesis of Aspergillus fumigatus," Eukaryotic Cell, 7:7, 1535-9778 (2008).
Devereux et al., "A comprehensive set of sequence analysis programs for the VAX," Nucleic Acids Res. 12:387-95 (1984).
Feng et al., "Progressive Sequence Alignment as a Prerequisite to Correct Phylogenetic Trees," J. Mol. Evol. 35:351-60 (1987).
Garcia et al., "The Global Transcriptional Response to Transient Cell Wall Damage in *Saccharomyces cerevisiae* and Its Regulation by the Cell Integrity Signaling Pathway," J. Biol. Chem. 279:15183-15195 (2004).
Hagiwara, D. et al., "Functional analysis of C2H2 zinc finger transcription factor CrzA involved in calcium signaling in Aspergillus nidulans," Current Genetics, 54:6, 325-338 (2008).
Henikoff et al., "Amino acid substitution matrices from protein blocks," Proc. Natl. Acad. Sci. USA 89:10915) (1989).
Higgins et al., "CLUSTAL: a package for performing multiple sequence alignment on a microcomputer," Gene 73:237-244) (1988).
Higgins et al., "Fast and sensitive multiple sequence alignments on a microcomputer," CABIOS Communication, 5:151-53 (1989).
Hughes et al., "Assembly, organization, and function of the COPII coat," Cell. Biol. 129:129-51 (2008).
Karababa et al., "CRZ1, a target of the calcineurin pathway in Candida albicans," Mol. Microbiol. 59:1429-1451 (2006).
Karhinen, L. et al., "Endoplasmic Reticulum Exit of a Secretory Glycoprotein in the Absence of Sec24p Family Proteins in Yeast," Traffic 6:562-74 (2005).
Karlin et al., "Applications and statistics for multiple high-scoring segments in molecular sequences,"(Proc. Natl. Acad. Sci. USA 90:5873-87) (1993).

(Continued)

*Primary Examiner* — Rodney P Swartz
(74) *Attorney, Agent, or Firm* — Danisco US Inc.

(57) ABSTRACT

Described are compositions and methods relating to variant filamentous fungi having altered growth characteristics. Such variants are well-suited for growth in submerged cultures, e.g., for the large-scale production of enzymes and other proteins for commercial applications.

36 Claims, 1 Drawing Sheet

(56) References Cited

OTHER PUBLICATIONS

Kothe, G., Calcineurin Subunit B Is Required for Normal Vegetative Growth in Neurospora crassa, Fungal Genet. Biol 23:248-258 (1998).
Lagorce et al., "Genome wide analysis of the response to cell wall mutations in the yeast *S.cerevisiae*," J. Biol.Chem. 278:20345-20357 (2003).
Mouyna, I. et al., "Deletion of GEL2 encoding for a β(1-3)glucanosyltransferase affects morphogenesis and virulence in Aspergillus fumigatus," Molecular Microbiol 56(6), 1675-1688 (2005).
Munro, C. et al., "The PKC, HOG and Ca2+ signalling pathways co-ordinately regulate chitin synthesis in Candida albicans," Mol. Microbiol. 63:1399-1413, (2007).
Needleman et al., "A General Method Applicable to the Search for Similarities in the Amino Acid Sequence of Two Proteins," J. Mol. Biol., 48:443 (1970).
Pardini et al. , "The CRH Family Coding for Cell Wall Glycosylphosphatidylinositol Proteins with a Predicted Transglycosidase Domain Affects Cell Wall Organization and Virulence of Candida albicans," J. Biol. Chem.
Passolunghi, S. et al., "Cloning of the Zygosaccharomyces bailii GAS1 homologue and effect of cell wall engineering on protein secretoryphenotype," Microbial Cell Factories 9:7-17 (2010).
Pearson et al., Improved tools for biological sequence comparison, Proc. Natl. Acad. Sci. USA 85:2444 (1988).
Peng, R. et al., "Evidence for Overlapping and Distinct Functions in Protein Transport of Coat Protein Sec24p Family Members," J. Biol.Chem. 275:11521-28 (2000).
Peterbauer, C. et al., The Trichoderma atroviride seb1 (stress response element binding) gene encodes an AGGGG•binding protein which is involved.
Prokisch, H., et al., "Impairment of calcineurin function in Neurospora crassa reveals its essential role in hyphal growth, morphology and maintenance of the apical Ca2+ gradient," Mol. Gen. Genet. 256:104-114 (1997).

Roberg, K.J. et al., "*LST1* Is a *SEC24* Homologue Used for Selective Export of the Plasma Membrane ATPase from the Endoplasmic Reticulum," J. Cell. Biol. 145:659-72 (1999).
Schirawski, J. et al. "Endoplasmic reticulum glucosidase II is required for pathogenicity of *Ustilago maydis*,"(2005).
Schumacher, J. et al., "Calcineurin-responsive zinc finger transcription factor CRZI of Botrytis cinerea is required for growth, development, and full virulence on bean plants," Eukaryotic Cell, 7:4, 584-601 (2008).
Shimoni, Y. et al., "Lst1p and Sec24p Cooperate in Sorting of the Plasma Membrane ATPase into COPII Vesicles in *Saccharomyces cerevisiae*," J. Cell. Biol. 151:973-84 (2000).
Simola, M et al. "Trehalose is required for conformational repair of heat denatured proteins in the yeast endoplasmic reticulum but not for maintenance of membrane traffic functions after severe heat stress,".
Singer, M et al., Multiple Effects of Trehalose on Protein Folding In Vitro and In Vivo, Molecular Cell, vol. 1, 639-648, Apr. 1998.
Smith et al. "Comparison of Biosequences," Adv. Appl. Math. 2:482 (1981).
Soriani, FM et al., "Functional characterization of the Aspergillus fumigatus CRZ1 homologue, CrzA," Molecular Microbiology, 67:6, 1365-2958 (2008).
Spielvogel, A. et al., "Two zinc finger transcription factors, CrzA and SltA, are involved in cation homeostsis and detoxification in Aspergillus nidulans + supplementary online data," Biochemical Journal, 414:3, 419-429 (2008).
Talbot et al., "Identification andcharacterization of MPG1, a gene," the Plant Cell, vol. 5, No. 11, pp. 1575-1590, 1993.
Turchini, A. et al., Increase of External Osmolarity Reduces Morphogenetic Defects and Accumulation of Chitin in a gas1 Mutant of *Saccharomyces cerevisiae*J. Bacteriol. 182:1167-71 (2000).
WIPO, International Search Report for WO 2012/145596 (PCT/US2012/034405), 7 pages, published Oct. 26, 2012.
Yoshimoto et al., "Genome-wide Analysis of Gene Expression Regulated by the Calcineurin/Crz1p Signaling Pathway in *Saccharomyces cerevisiae*," J. Biol. Chem. 227:31079-31088 (2002).

\* cited by examiner

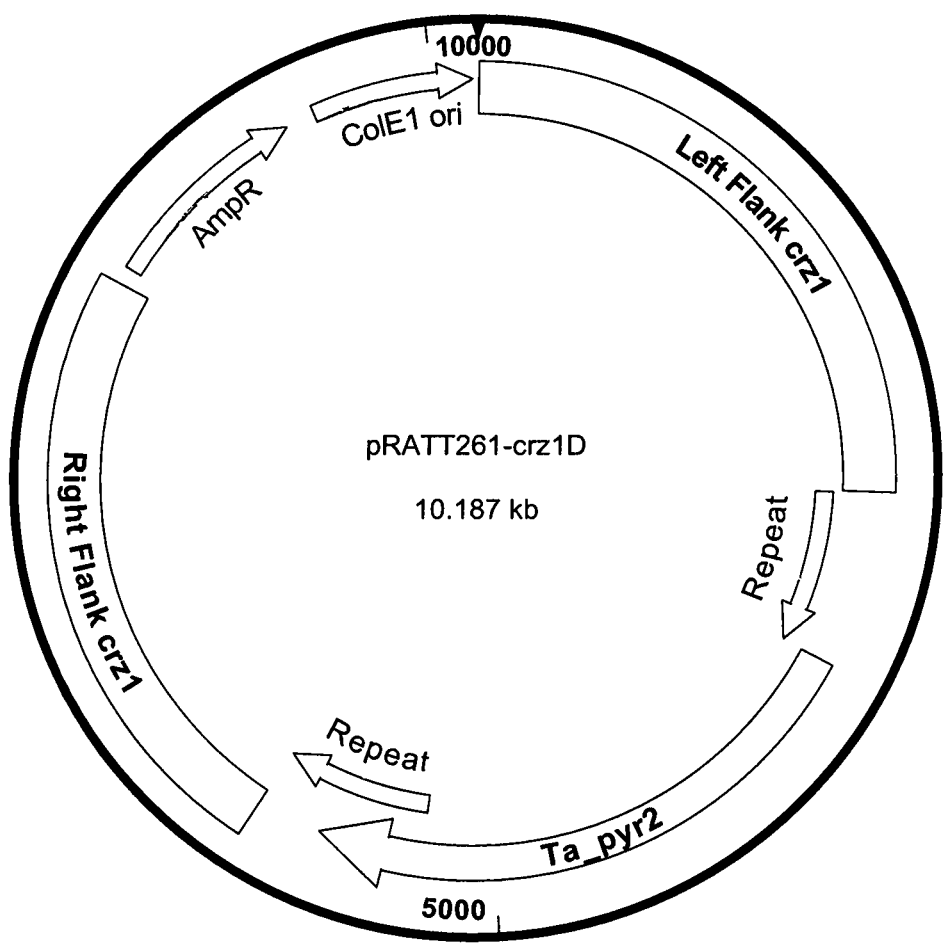

SEQUENCE LISTING

```
<160> NUMBER OF SEQ ID NOS: 13

<210> SEQ ID NO 1
<211> LENGTH: 668
<212> TYPE: PRT
<213> ORGANISM: Trichoderma reesei

<400> SEQUENCE: 1

Arg Gly Arg Ser Pro Ser Ala Gly Gly Phe Gln Ser Asp Ile Asn Gln
1               5                   10                  15

Ser His Ser Pro Ala Arg Ser Pro Leu Ala Pro Thr Asn Glu Gln Pro
            20                  25                  30

Ser Ala Gly Leu Gly Val Gly Leu Gly Gln Gln Gln Gln Arg Ala Phe
        35                  40                  45

Ala Ala Pro Leu His Pro Asn Tyr Asp Ser Phe Gly Ala Asn Gly Phe
    50                  55                  60

Leu Gly Ala Gln Ala Asn Ala Val Asp Pro Thr Asn Gly Phe Asp Pro
65                  70                  75                  80

Ser Ala Ser Phe Gly Gln Gln Pro Ala Thr Gly Pro Asp Ser Thr Leu
                85                  90                  95

Ser Leu Asn Ala Gln Ala Gln His Asn Tyr Leu Ser Pro Asn Leu His
            100                 105                 110

Asp Gly Asp Phe Ser Leu Phe Pro Ser Ala Ala Glu Gln Gly Asp Gln
        115                 120                 125

Tyr Asn Ala Pro Leu Phe Glu Gln Pro Pro Leu Gly Asp Leu Asn Ala
    130                 135                 140

Met Thr Ser Pro His Ser His Gln Ser Pro Thr Pro Pro Gln Leu Phe
145                 150                 155                 160

Gln Pro Asp Ser Leu Gln Ser Pro Pro Phe Asn Arg His Gln Phe Ser
                165                 170                 175

Ser Pro Pro Thr His Ser Arg Asn Ala Ser Leu Gly Pro Glu Ala Ala
```

-continued

```
                180             185                 190
Leu Leu Pro Ser Gln Ile Gly Asp Trp Thr Gln Pro Gln Phe Gln Gly
            195                 200             205

His Arg Arg Thr Pro Ser Glu Tyr Ser Asp Val Ser Ser Val Ala Pro
            210                 215             220

Ser Pro His Leu Val Ser Ser Asp Thr Phe Asp Ala Asp Gln Ser Gly
225                 230                 235                 240

His Ser Pro Leu Gln Arg Pro Ala Asp Val Ser Leu Tyr Gln Glu Val
                245                 250                 255

Leu Gly Ile Gly Ser Phe Ser Leu Ala Asp His Gly Ser Pro Gly Tyr
            260                 265                 270

His Gly Arg Ser Pro Ser His Ser Pro Ala Ile Ser Pro Arg Ile Met
            275                 280                 285

Pro Gln Gln Met Pro Asp Thr Met Gln Pro Ser Phe Asn Leu Ile Pro
            290                 295                 300

Pro Asn Gly Gly Phe Asp Gly Val Ser Gly Tyr Pro Asp Leu Gln Pro
305                 310                 315                 320

Ser His Glu Ser Phe Pro Ser Leu Ser Gly Gly Met Gly Gly Asp Met
                325                 330                 335

His Gln Met Ala Pro Pro Ala Ile Asn Ile Asp Phe Ala Pro Thr Asn
            340                 345                 350

Ser Arg Gln Gly Ser Phe Glu Pro Pro Lys Ser Gln Met Asp Gln Asp
            355                 360                 365

Ser Leu Thr Pro Pro Glu Arg Gly Arg Pro Lys Ser Arg Pro Arg Ala
            370                 375                 380

Val Thr Asp Pro Phe His Pro Gly Ser Gly Ile Leu Pro Pro Gly Asn
385                 390                 395                 400

Leu Gly Ser Ser Leu Gly Val Asp Leu Ala Ala Arg Ser Asp Thr Ala
                405                 410                 415

Ser Arg Ser Leu Ser Pro Leu Asp Arg Ser Gly Thr Ser Ser Pro Ala
            420                 425                 430

Ser Arg Arg Arg Gln Ser Thr Ser Ser Val Pro Asn Asn Val Ile Ala
            435                 440                 445

Leu Arg Leu Ala Asp Pro Glu Tyr Gln Asn Ser Gln Glu Ala Gly Thr
            450                 455                 460

Ser Lys Arg Met Gln Lys His Pro Ala Thr Phe Gln Cys Thr Leu Cys
465                 470                 475                 480

Pro Lys Arg Phe Thr Arg Ala Tyr Asn Leu Arg Ser His Leu Arg Thr
                485                 490                 495

His Thr Asp Glu Arg Pro Phe Val Cys Thr Val Cys Gly Lys Ala Phe
            500                 505                 510

Ala Arg Gln His Asp Arg Lys Arg His Glu Ser Leu His Ser Gly Glu
            515                 520                 525

Lys Lys Phe Val Cys Lys Gly Asp Leu Lys Thr Gly Gly Gln Trp Gly
            530                 535                 540

Cys Gly Arg Arg Phe Ala Arg Ala Asp Ala Leu Gly Arg His Phe Arg
545                 550                 555                 560

Ser Glu Ala Gly Arg Ile Cys Ile Lys Pro Leu Leu Asp Glu Glu Met
                565                 570                 575

Val Glu Arg Gln Arg Gln Trp Gln Glu Gln Arg Met Gln Gln Asn Met
            580                 585                 590

Ala Gln Asn Met Ala Asn Pro Gln Val Met Gly Met Asp Ala Gly Pro
            595                 600                 605
```

```
Ala Tyr Pro Met Asp Ala Ser Gly Asn Tyr Thr Leu Pro Gln Ala Leu
            610                 615                 620

Leu Ala Gln Tyr Pro Ala Leu Ala Gln Met Asn Trp Ser Ala Thr Asp
625                 630                 635                 640

Met Gly Gly Gly Leu Asp Asp Glu Leu Ser Gly Arg Ser Ser Phe Asp
                    645                 650                 655

Ala Ser Asp Tyr Asp Asp Gly Asp Gly Gly Tyr
            660                 665

<210> SEQ ID NO 2
<211> LENGTH: 730
<212> TYPE: PRT
<213> ORGANISM: Emericella nidulans

<400> SEQUENCE: 2

Met Asp Pro Gln Asp Thr Leu Gln Asp Leu Gly Gln Ala Pro Ala Ala
1               5                   10                  15

His Ile Asn Arg Ser Ala Ser Pro Ser Ala His Ala His Gln Gln Tyr
                20                  25                  30

Asn Asn Asn His Asn Asp Leu Thr Ile Asp Pro Ser Val Thr Ser Asn
            35                  40                  45

Ser Ser Tyr Pro Pro Ser Ser Phe Ala Asn Ser Ala Pro Gly Ser
    50                  55                  60

Glu Ala Phe Ala Tyr Ser Ser Tyr Leu Thr Pro Ala Thr Ala Thr
65                  70                  75                  80

Asp His Asn Phe Ala Arg Pro Ser Leu Gln Ile Pro Gln Ser Phe Asp
                85                  90                  95

Gln Gly Leu Ser His Gln Pro Ala Glu Glu Asn Phe Ser Asn Leu Leu
            100                 105                 110

Asn Ser Asn Thr Gly Asp Phe Asp Phe Ser Leu Tyr Gln Gly Ser Ser
        115                 120                 125

Pro Asn Asn Thr Gly Ser Asp Tyr Pro Ser Ser Gly Leu Leu Asp Pro
    130                 135                 140

Gln Gln Ser Gly Asn Gln Ala Val Asn Pro Val Asp Leu Val Ser Gln
145                 150                 155                 160

Ile Pro Ser Pro His Pro Ser Asn Ser Ser Gln Thr Ser Pro Leu Asp
                165                 170                 175

Gln Pro Pro Ser Ser Ala Met Ser Pro Pro Ala Ser Ser Pro Gly Thr
            180                 185                 190

Phe Tyr Thr Pro Gln His Ser Arg His Thr Ser Leu Asp Pro Ala Ser
        195                 200                 205

Ala Ala Tyr Met Thr Asn Val Ser His Pro Glu Trp Gln Ala Val Met
    210                 215                 220

Asn Asn Ser Ala Phe His Gly His Arg Arg Ala Pro Ser Glu Val Ser
225                 230                 235                 240

Glu Val Ser Ser Ala Ala His Ser Pro Tyr Leu Pro Gln His Asp Ser
                245                 250                 255

Phe Asp Val Ala Asp Asn Asn Pro Ser Pro Leu Leu Ala Ala Gln Asn
            260                 265                 270

Asp Pro Ser Leu Tyr Asp Asn Ala Ala Leu Gly Ile Glu Ser Phe Thr
        275                 280                 285

Leu Ser Glu His His Gln Pro Gln Thr Gln Gly Ile Ser Pro His His
    290                 295                 300

Ser Pro Tyr Ile Ser Pro Gln Leu Met Pro Gln His Pro Thr Asp Ile
```

```
            305                 310                 315                 320
Ile Pro Gly Gly Pro Phe Ile Ser Ala Pro Ala Thr Asn Ser Ala Tyr
            325                 330                 335
Pro Thr Pro Pro Thr Glu Gly Tyr Pro Asn Gly Gly Asp Ile Gly Gln
            340                 345                 350
Ala Ser Gln Met Ala Pro Pro Ser Ile Asn Val Glu Phe Ala Pro Pro
            355                 360                 365
Ala Lys Ala Gln Val Phe Pro Pro Glu Lys Ser Thr Ala Asp Met Asp
            370                 375                 380
Ser Leu Ser Pro Pro Ser Leu Arg Thr Ser Arg Met Arg Ser Lys
385                 390                 395                 400
Ser Asp Pro Tyr Ala Val Ser Ile Ser Arg Pro Arg Ser Pro Ser Ser
            405                 410                 415
Pro Ser Ala Ser Leu Asp Ala Leu Ala Ala Ser Ser Pro Arg Ser Leu
            420                 425                 430
Ser Pro Phe Asn Val Gly Arg His Pro Tyr Ser Asn Pro Ser Ser Arg
            435                 440                 445
Glu Pro Ser Pro Ala Arg Ser Ala Arg Arg Leu Ser Thr Ser Ser Val
            450                 455                 460
Asp Ser Arg Asn Tyr Ile Leu Gly Leu Ala Asp Pro Gln Arg Pro Gly
465                 470                 475                 480
Ser Asn Asn Thr Asp Ser Lys Arg Val Gln Lys His Pro Ala Thr Phe
            485                 490                 495
Gln Cys Thr Leu Cys Pro Lys Arg Phe Thr Arg Ala Tyr Asn Leu Arg
            500                 505                 510
Ser His Leu Arg Thr His Thr Asp Glu Arg Pro Phe Val Cys Thr Val
            515                 520                 525
Cys Gly Lys Ala Phe Ala Arg Gln His Asp Arg Lys Arg His Glu Gly
            530                 535                 540
Leu His Ser Gly Glu Lys Lys Phe Val Cys Arg Gly Asp Leu Ser Arg
545                 550                 555                 560
Gly Gly Gln Trp Gly Cys Gly Arg Arg Phe Ala Arg Ala Asp Ala Leu
            565                 570                 575
Gly Arg His Phe Arg Ser Glu Ala Gly Arg Ile Cys Ile Lys Pro Leu
            580                 585                 590
Leu Asp Glu Glu Ser Gln Glu Arg Glu Arg Thr Leu Ile Asn Gln Gln
            595                 600                 605
Gln Gln His Leu Gln Pro Val Asn Gln Pro Leu Met Leu Pro Gly Gln
            610                 615                 620
Gly Thr Glu Ala Gln His Thr Gly Ser Phe Ile Leu Pro Ala Ala Leu
625                 630                 635                 640
Leu Ala Gln Tyr Pro Ala Leu Gln Thr Leu Gln Trp Asp Gln Ile Pro
            645                 650                 655
Ala Gly Thr Asp Asp Thr Ser Asp Ile Gly Gly Arg Asn Ser Phe Asp
            660                 665                 670
Ala Ser Ser Gly Gly Glu Phe Gly Phe Asp Asp Glu Ser Gly Ile
            675                 680                 685
Ser Val Ser Gly Met Ser Thr Gly Tyr Ala Ser Asp Gln Gly Asn Ile
            690                 695                 700
Tyr Asn Val Asp Ala Gln Gly Gln Met Leu Gly Val Asn Pro Gly Glu
705                 710                 715                 720
Ala Gly Tyr Ala Asn Pro Asn Trp Gly Lys
            725                 730
```

<210> SEQ ID NO 3
<211> LENGTH: 678
<212> TYPE: PRT
<213> ORGANISM: Saccharomyces cerevisiae

<400> SEQUENCE: 3

```
Met Ser Phe Ser Asn Gly Asn Met Ala Ser Tyr Met Thr Ser Ser Asn
1               5                   10                  15

Gly Glu Glu Gln Ser Ile Asn Asn Lys Asn Asp Ile Asp Asp Asn Ser
            20                  25                  30

Ala Tyr Arg Arg Asn Asn Phe Arg Asn Ser Ser Asn Ser Gly Ser His
        35                  40                  45

Thr Phe Gln Leu Ser Asp Leu Asp Leu Asp Val Asp Met Arg Met Asp
    50                  55                  60

Ser Ala Asn Ser Ser Glu Lys Ile Ser Lys Asn Leu Ser Ser Gly Ile
65                  70                  75                  80

Pro Asp Ser Phe Asp Ser Asn Val Asn Ser Leu Leu Ser Pro Ser Ser
                85                  90                  95

Gly Ser Tyr Ser Ala Asp Leu Asn Tyr Gln Ser Leu Tyr Lys Pro Asp
            100                 105                 110

Leu Pro Gln Gln Gln Leu Gln Gln Gln Gln Leu Gln Gln Gln Gln Gln
        115                 120                 125

Gln Gln Gln Gln Gln Gln Gln Gln Lys Gln Thr Pro Thr Leu
    130                 135                 140

Lys Val Glu Gln Ser Asp Thr Phe Gln Trp Asp Asp Ile Leu Thr Pro
145                 150                 155                 160

Ala Asp Asn Gln His Arg Pro Ser Leu Thr Asn Gln Phe Leu Ser Pro
                165                 170                 175

Arg Ser Asn Tyr Asp Gly Thr Thr Arg Ser Ser Gly Ile Asp Ser Asn
            180                 185                 190

Tyr Ser Asp Thr Glu Ser Asn Tyr His Thr Pro Tyr Leu Tyr Pro Gln
        195                 200                 205

Asp Leu Val Ser Ser Pro Ala Met Ser His Leu Thr Ala Asn Asn Asp
    210                 215                 220

Asp Phe Asp Asp Leu Leu Ser Val Ala Ser Met Asn Ser Asn Tyr Leu
225                 230                 235                 240

Leu Pro Val Asn Ser His Gly Tyr Lys His Ile Ser Asn Leu Asp Glu
                245                 250                 255

Leu Asp Asp Leu Leu Ser Leu Thr Tyr Ser Asp Asn Asn Leu Leu Ser
            260                 265                 270

Ala Ser Asn Asn Ser Asp Phe Asn Asn Ser Asn Asn Gly Ile Ile Asn
        275                 280                 285

Thr Ala Asp Thr Gln Asn Ser Thr Ile Ala Ile Asn Lys Ser Lys Val
    290                 295                 300

Gly Thr Asn Gln Lys Met Leu Leu Thr Ile Pro Thr Ser Ser Thr Pro
305                 310                 315                 320

Ser Pro Ser Thr His Ala Ala Pro Val Thr Pro Ile Ile Ser Ile Gln
                325                 330                 335

Glu Phe Asn Glu Gly His Phe Pro Val Lys Asn Glu Asp Asp Gly Thr
            340                 345                 350

Leu Gln Leu Lys Val Arg Asp Asn Glu Ser Tyr Ser Ala Thr Asn Asn
        355                 360                 365

Asn Asn Leu Leu Arg Pro Asp Asp Asn Asp Tyr Asn Asn Glu Ala Leu
```

```
                      370                 375                 380
Ser Asp Ile Asp Arg Ser Phe Glu Asp Ile Ile Asn Gly Arg Lys Leu
385                 390                 395                 400

Lys Leu Lys Lys Ser Arg Arg Ser Ser Gln Thr Ser Asn Asn Ser
            405                 410                 415

Phe Thr Ser Arg Arg Ser Arg Ser Arg Ser Ile Ser Pro Asp Glu
                420                 425                 430

Lys Ala Lys Ser Ile Ser Ala Asn Arg Glu Lys Leu Leu Glu Met Ala
            435                 440                 445

Asp Leu Leu Pro Ser Ser Glu Asn Asp Asn Asn Arg Glu Arg Tyr Asp
            450                 455                 460

Asn Asp Ser Lys Thr Ser Tyr Asn Thr Ile Asn Ser Ser Asn Phe Asn
465                 470                 475                 480

Glu Asp Asn Asn Asn Asn Leu Leu Thr Ser Lys Pro Lys Ile Glu
                485                 490                 495

Ser Gly Ile Val Asn Ile Lys Asn Glu Leu Asp Asp Thr Ser Lys Asp
                500                 505                 510

Leu Gly Ile Leu Leu Asp Ile Asp Ser Leu Gly Gln Phe Glu Gln Lys
            515                 520                 525

Val Gly Phe Lys Asn Asp Asn His Glu Asn Asn Asp Asn Gly Thr
            530                 535                 540

Phe Ser Val Lys Lys Asn Asp Asn Leu Glu Lys Leu Asp Ser Val Thr
545                 550                 555                 560

Asn Asn Arg Lys Asn Pro Ala Asn Phe Ala Cys Asp Val Cys Gly Lys
                565                 570                 575

Lys Phe Thr Arg Pro Tyr Asn Leu Lys Ser His Leu Arg Thr His Thr
            580                 585                 590

Asn Glu Arg Pro Phe Ile Cys Ser Ile Cys Gly Lys Ala Phe Ala Arg
            595                 600                 605

Gln His Asp Arg Lys Arg His Glu Asp Leu His Thr Gly Lys Lys Arg
            610                 615                 620

Tyr Val Cys Gly Gly Lys Leu Lys Asp Gly Lys Pro Trp Gly Cys Gly
625                 630                 635                 640

Lys Lys Phe Ala Arg Ser Asp Ala Leu Gly Arg His Phe Lys Thr Glu
                645                 650                 655

Ser Gly Arg Arg Cys Ile Thr Pro Leu Tyr Glu Glu Ala Arg Gln Glu
            660                 665                 670

Lys Ser Gly Gln Glu Ser
            675

<210> SEQ ID NO 4
<211> LENGTH: 754
<212> TYPE: PRT
<213> ORGANISM: Aspergillus fumigatus

<400> SEQUENCE: 4

Met Ala Ser Gln Glu Met Phe Pro Glu Leu Gly Gln Ser Pro Ala Pro
1               5                   10                  15

Gly Val Lys Ser Arg Gly Val Ser Arg Ser Pro His Pro His Gln Gln
            20                  25                  30

Gln Gln Gln Gln Gln His Gln Gln His Gln Gly Gln Phe Thr Gly Thr
        35                  40                  45

Val Thr Gly Leu Asp Leu Asp Ser Ser Ile Ala Thr Ala Ser Ser Phe
    50                  55                  60
```

```
Ala Asn Ser Ser Phe Asp Pro Asn Ser Asn Asn Val Ser Pro Ser Ala
 65                  70                  75                  80

Glu Ser Tyr Gly Tyr Thr Ala Ala Gly Tyr Leu Ser Gly Thr Pro Ala
             85                  90                  95

Ser Gln Thr Asp Gln Asn Tyr Ala Asn Ser Leu Gln Ile Pro Gln Ser
            100                 105                 110

Tyr Gly Thr Gly Leu Val Pro Gln Phe Asn Glu Ser Arg Gly Leu Pro
        115                 120                 125

Ile Gln Gln Ser Gln Gln Gln His His Gln Gln Pro Ser Leu Asp
        130                 135                 140

Asp Asn Phe Ser Asp Leu Leu Asn Ser Asn Ala Thr Glu Tyr Asp Phe
145                 150                 155                 160

Asn Thr Val Tyr Gln Thr His Ser Pro Ser Ser Asn Thr Ala Pro Glu
                165                 170                 175

Tyr Asp Ser Ser Leu Leu Leu Asp Pro Gln Val His Gln Gln Ser His
            180                 185                 190

Pro Thr Gln Ile Pro Ser Ser His Ser Ser Thr Ser Pro Gln Ile Ser
        195                 200                 205

Pro Leu Glu Gln Gln Gln His Ser Ser Pro Gly Pro Met Ser Thr Gln
210                 215                 220

Gly Ser Thr Thr Val Ala Tyr Tyr Thr Pro Gln His Ser Arg His Ala
225                 230                 235                 240

Ser Leu Asp Pro Ala Thr Ala Ala Phe Leu Thr Ser Asn Thr His Pro
                245                 250                 255

Asp Trp Gln Ala Val Met Gly Asn Ser Ala Ala Phe Gln Gly His Arg
            260                 265                 270

Arg Ala Pro Ser Glu Val Ser Glu Ile Ser Ser Ala Ala Pro Ser Pro
        275                 280                 285

Tyr Leu Ser Gln His Glu Ser Phe Asp Gly Val Asp Asn Asn Pro Ser
290                 295                 300

Pro Leu Leu Ala Pro Gln Asn Asp Pro Ser Leu Tyr Asp Ser Ala Leu
305                 310                 315                 320

Gly Ile Glu Asn Phe Thr Leu Ser Glu Gln His Gln Gln His Gln Gly
                325                 330                 335

Phe Ser Pro Ala His Ser Pro Tyr Ile Ser Pro Arg Leu Met Pro Gln
            340                 345                 350

Gln Gly Gln Glu Met Met Pro Asn Val Pro Tyr Leu Ser Gly Pro Ala
        355                 360                 365

Pro Asn Thr Gln Tyr Pro Thr Pro Pro Asn Asp Met Tyr Gly Asn Gly
        370                 375                 380

Ala Glu Gly Met Met Asn Met Ser Gln Gly Thr His Pro Ser Val Asp
385                 390                 395                 400

Ile Gly Gln Ala Ser Gln Met Ala Pro Pro Ser Ile Asn Val Glu Phe
                405                 410                 415

Ala Pro Pro Ser Arg Ile Pro Ser Phe Gly Pro Ser Lys Pro Ala Ser
            420                 425                 430

Asn Leu Asp Ser Leu Ser Pro Pro Ser Ser Thr Arg Ser Arg Gly
        435                 440                 445

Arg Ser Lys Ser Asp Pro Tyr Ala His Pro Ser Thr Ser Arg Leu Arg
        450                 455                 460

Ser Ser Ser Thr Ser Ser Ser Leu Asp Pro Leu Ala Pro Thr Thr Pro
465                 470                 475                 480

Arg Ser Leu Ser Pro Phe Asp Ser Phe Gly Arg Gln Gln Gln Ser Asn
```

```
                  485                 490                 495
Pro Ser Ser Arg Asp Pro Ser Pro Ser Arg Ser Asn Arg Arg Leu Ser
                500                 505                 510

Thr Ser Ser Ile Asp Ser Arg Asn Tyr Ile Leu Gly Leu Ala Asp Pro
            515                 520                 525

Gln Arg Pro Gly Ala Ser Pro Asn Asp Ser Lys Arg Val Gln Lys His
530                 535                 540

Pro Ala Thr Phe Gln Cys Asn Leu Cys Pro Lys Arg Phe Thr Arg Ala
545                 550                 555                 560

Tyr Asn Leu Arg Ser His Leu Arg Thr His Thr Asp Glu Arg Pro Phe
                565                 570                 575

Val Cys Thr Val Cys Gly Lys Ala Phe Ala Arg Gln His Asp Arg Lys
            580                 585                 590

Arg His Glu Gly Leu His Ser Gly Glu Lys Lys Phe Val Cys Gln Gly
        595                 600                 605

Glu Leu Ser Arg Gly Gly Gln Trp Gly Cys Gly Arg Arg Phe Ala Arg
    610                 615                 620

Ala Asp Ala Leu Gly Arg His Phe Arg Ser Glu Ala Gly Arg Ile Cys
625                 630                 635                 640

Ile Lys Pro Leu Leu Asp Glu Glu Ser Gln Glu Arg Glu Arg Ser Leu
                645                 650                 655

Met Asp Gln Gln Gln His His Leu Gln Pro Leu Pro Gln Gln Val Met
            660                 665                 670

Val Pro Val Asp Asn Pro His Ala Gly Asn Phe Val Leu Pro Ala Ala
        675                 680                 685

Leu Leu Ala Gln Tyr Pro Ala Leu Gln Thr Leu Gln Trp Asp Gln Ile
    690                 695                 700

Ala Ala Ser Ala Asp Asp Pro Ser Asp Ile Gly Gly Arg Ser Ser Phe
705                 710                 715                 720

Asp Ala Ser Ser Gly Asn Glu Phe Gly Phe Glu Asp Asp Ser Gly
                725                 730                 735

Leu Ser Ser Val Ser Gly Ile Asn Ala Gly Tyr Ser Ala Ala Gly Asn
            740                 745                 750

Phe Tyr

<210> SEQ ID NO 5
<211> LENGTH: 768
<212> TYPE: PRT
<213> ORGANISM: Penicillium marneffei

<400> SEQUENCE: 5

Met Glu Asn His Gly Gln Tyr Ala Asn Arg Gly Arg Ser Pro Ser Ala
1               5                   10                  15

Ser Val His Ser Arg Asn Val Ser Pro Ser His Gly Gln His
            20                  25                  30

Ser Pro Tyr His Asp Pro Ser Ala Ala Gly Leu Met Leu Asp Ala Ser
        35                  40                  45

Thr Ala Gly Thr Gly Tyr Gln Ser Asn Leu Thr Phe Thr Thr Ala Pro
    50                  55                  60

Pro Leu Ser Ser Ser Leu Ala Pro Asp Ser Asn Pro Asp Leu Tyr
65                  70                  75                  80

Asn Asn Phe Leu Thr Ala Thr Thr Ser Gln Gln His Asp Ser Leu
                85                  90                  95

Ala Ala Gln Asn Asp Gln Phe Ala Ser Ser Val Ala Ala Thr Phe Gln
```

```
                100             105             110
Asp Gln Leu Asp Gln Ser Ala Thr His Gln Asp Ala Asn Tyr Ser Asn
            115                 120                 125

Leu Leu Asn Pro Asn Pro Asn Asp Tyr Asp Phe Thr Gln Tyr Ala Val
130             135                 140

Gly Gly Asp Asn Ala Val Met Gln Ser Ala Phe Asp Ser Ser Leu Leu
145                 150                 155                 160

Leu Asp Gln Gln Gln Gln Gln Gln Gln Gln Gln Gln His Asn Thr
            165                 170                 175

Gln Asn Val Gln Leu Met Gly Gln Gly Asp Met Thr Gln Met Gly Ser
            180                 185                 190

Pro Asn Asn Leu Leu Ser Pro Glu His His Ser Ser Pro Gly Asn Ser
            195                 200                 205

His Thr Ser Pro Pro Ile Ser Ser Gly Pro Phe Tyr Ser Pro Gly His
            210                 215                 220

Ser Arg Ser Ala Ser Leu Asp Pro Met Ser Ala Ala Tyr Met Ser Asn
225                 230                 235                 240

His Asn Gln Ala Gln Asp Trp Lys Asn Met Leu Glu Asn His Ser Phe
                245                 250                 255

Gln Ser His Arg Arg Ala Pro Ser Glu His Ser Asp Val Ser Ser Val
                260                 265                 270

Ala His Ser Pro Tyr Ala Gly His His Glu Ser Phe Asp Ala Leu Asp
            275                 280                 285

Gly Ala Ser Pro Ser Leu Gly Ala Gln Asn Asp Pro Val Leu Tyr Asp
            290                 295                 300

Asn Thr Leu Ala Met Asp Ser Phe Thr Leu Ser Glu Gln Gln Gln Gly
305                 310                 315                 320

Leu Ser Pro His His Ser Pro Tyr Ile Ser Pro Gln Met Pro Ser Gln
                325                 330                 335

Asp Ile Thr Ser Asp Ala Phe Ile Leu Ser Gly Gln Gln Asn Met Thr
                340                 345                 350

Gln Phe Pro Thr Leu Pro His Asp Ile Phe Thr Gly Gln Pro Asp Asp
                355                 360                 365

Gly Met Leu Ala Gly Thr Gln Ala Pro Asp Met Ser Gly Leu Asp Ala
            370                 375                 380

Asn Gln Met Asn Asn Met Val Pro Pro Ser Ile Asn Val Glu Phe
385                 390                 395                 400

Ala Pro Pro Ser Arg Met Pro Ser Phe Gly Pro Gly Glu Asn Asp
                405                 410                 415

Phe Asp Ala Leu Ser Pro Pro Ser Arg Gly Ser Arg Gly Arg Ser Lys
                420                 425                 430

Ser Asp Pro Phe Gly Arg Pro Thr Pro Ile Val Arg Pro His Ser Gln
            435                 440                 445

Ser Val Ser Ser Thr Ser Ser Leu Asp Pro Ala Val Gly Ser Ser Pro
            450                 455                 460

Arg Ser Leu Ser Pro Phe Asp Ser Met Gly Gly Ser Arg Ser Asn Pro
465                 470                 475                 480

Gly Ser Arg Gly Val Ser Pro Ala Ser Arg Ser Ser Ile Arg Arg Gln
                485                 490                 495

Ser Thr Ser Ser Ile Glu Arg Lys Val Ile Leu Asp Leu Ala Asp Pro
            500                 505                 510

Gln Arg Pro Gly Ala Thr Pro Gly Glu Ser Lys Arg Thr Gln Lys His
            515                 520                 525
```

Pro Ala Thr Phe Gln Cys Asn Leu Cys Pro Lys Arg Phe Thr Arg Ala
        530                 535                 540

Tyr Asn Leu Arg Ser His Leu Arg Thr His Thr Asp Glu Arg Pro Phe
545                 550                 555                 560

Val Cys Thr Val Cys Gly Lys Ala Phe Ala Arg Gln His Asp Arg Lys
                565                 570                 575

Arg His Glu Gly Leu His Ser Gly Glu Lys Lys Phe Val Cys Arg Gly
            580                 585                 590

Asp Leu Ala Ser Arg Gly Gln Trp Gly Cys Gly Arg Arg Phe Ala Arg
        595                 600                 605

Ala Asp Ala Leu Gly Arg His Phe Arg Ser Glu Ala Gly Arg Ala Cys
    610                 615                 620

Ile Lys Ala Leu Leu Asp Glu Glu Ala Ile Glu Arg Asn Arg Ile Phe
625                 630                 635                 640

Met Glu Gln Gln Ala Gln Gln Ala Gln Gln His Leu Gln Pro
            645                 650                 655

Val Pro Gln Pro Leu Met Val Pro Gly Leu Asp Asn Gln Ala Gly Phe
                660                 665                 670

Thr Leu Pro Ala Ala Leu Leu Ala Gln Tyr Pro Ala Leu Gln Asn Leu
            675                 680                 685

Gln Trp Asp Gln Ile Ala Thr Ser Gly Thr Asp Val Ser Asp Ile
    690                 695                 700

Ser Ala Arg Asn Ser Phe Asp Ala Gly Ser Gly Glu Phe Gly Phe
705                 710                 715                 720

Asp Asp Asp Asp Leu Ser Ile Gly Ser Phe Thr Gly Ala Ser Gly Gln
                725                 730                 735

Gly Val Ile Tyr Ala Gly Gly Ser His Pro Thr Ser Ala Pro Asn Phe
            740                 745                 750

Ala Leu Glu Ala Thr Asp Pro Asn Phe Thr Gly Gln Glu Trp Ser Gln
        755                 760                 765

<210> SEQ ID NO 6
<211> LENGTH: 773
<212> TYPE: PRT
<213> ORGANISM: Aspergillus flavus

<400> SEQUENCE: 6

Met Ala Ser Gln Asp Thr Leu Arg Asp Ala Gly Gln Ser Thr Ala Asp
1               5                   10                  15

Val Lys Asn Arg Ser Val Ser Pro Ser Ala His Pro Gln His Gln Tyr
            20                  25                  30

Asn Asn Ala Ser Pro Gly Leu Thr Leu Asp Pro Ser Phe Thr Val Ser
        35                  40                  45

Ser Phe Gln Asn Ser Ala Ser Phe Asn Ala Asn Pro Asn Ser Asn Ser
    50                  55                  60

Pro Gly Ala Asp Ser Tyr Ser Tyr Thr Ala Gly Gly Tyr Leu Ser Pro
65                  70                  75                  80

Thr Ser Ala Gln Thr Leu Ala Pro Pro Asp Gln Ala Phe Ser His Ser
                85                  90                  95

Leu Gln Leu Gln Ser Phe Asp Pro Gly Leu Val Asn Gln Leu Asp His
            100                 105                 110

Ser Ser Gly Leu Ser Met Gln Pro Gln Leu Gln Gln His Gln Gln Pro
        115                 120                 125

His Glu Glu Asn Phe Ser Thr Leu Leu Asn Ser Asn Pro Thr Asp Phe

```
            130                 135                 140
Asp Phe Ser Leu Tyr Pro Asn His Ser Pro Asn Ser Thr Thr Ala Ser
145                 150                 155                 160

Glu Tyr Asp Ser Ser Leu Met Leu Asp Thr Gln Met Gln Gly His Pro
                165                 170                 175

Gln Gln Val Asn Gln Ala Val Asn Pro Val Asp Leu Ile Gly Gln Met
                180                 185                 190

Pro Ser Pro His Ser Val Thr Ser Pro Gln Met Ser Pro Gln Glu Gln
                195                 200                 205

Gln Pro His His Ser Ser Pro Gly Pro Met Ser Pro Pro Asn Ser Thr
            210                 215                 220

Pro Gly Ala Tyr Tyr Thr Pro Gln His Ser Arg His Thr Ser Leu Asp
225                 230                 235                 240

Pro Ala Ser Ala Ala Tyr Met Thr Gly Asn Ala Pro Pro Asp Trp Gln
                245                 250                 255

Ser Met Met Gly Asn Ala Ala Phe Gln Gly His Arg Arg Ala Pro Ser
                260                 265                 270

Glu Val Ser Glu Val Ser Ser Ala Ala Pro Ser Pro Tyr Met Ser His
            275                 280                 285

His Glu Ser Phe Asp Gly Val Asp Asn Asn Pro Ser Pro Leu Leu Ala
            290                 295                 300

Pro Gln Asn Asp Pro Gly Leu Tyr Asp Ser Ser Leu Gly Ile Glu Ser
305                 310                 315                 320

Phe Thr Leu Ser Glu Gln Gln Gln Gln Gln His Gln Gln Gly Ile
                325                 330                 335

Ser Pro Ile His Ser Pro Tyr Ile Ser Pro Gln Leu Met Pro Gln Gln
            340                 345                 350

Gly Asn Asp Leu Ile Pro Asn Met Pro Tyr Ile Ser Ala Pro Ala Gly
            355                 360                 365

Asn Arg Tyr Ser Cys Pro Pro Thr Asp Ile Tyr Gly Asn Gly Ala Glu
            370                 375                 380

Gly Val Ile Ser Met Pro Gln Gly Thr Ala Met Val Gly Asp Ile Gly
385                 390                 395                 400

Gln Ala Ser Gln Met Ala Pro Pro Ser Ile Asn Val Glu Phe Ala Pro
                405                 410                 415

Pro Ala Lys Asn Pro Ile Phe Pro Ala Lys Pro Ala Ala Asp Leu
            420                 425                 430

Asp Ser Leu Ser Pro Pro Ser Thr Arg Arg Met Arg Ser Lys Ser
            435                 440                 445

Asp Pro Tyr Ala His Pro Ala Ser Arg Ser Arg Ser Pro Val Ser Val
            450                 455                 460

Ser Ser Ser Leu Glu Pro Leu Ala Pro Ser Pro Arg Ser Leu Ser
465                 470                 475                 480

Pro Phe Asp Ser Thr Gly Arg Gln Pro His Ser Asn Pro Ser Ser Arg
                485                 490                 495

Glu Pro Ser Pro Ser Arg Ser Arg Arg Leu Ser Thr Ser Ser Ile Asp
                500                 505                 510

Asn Arg Asn Tyr Ile Leu Gly Leu Ala Asp Pro Gln Arg Pro Gly Ala
            515                 520                 525

Ser Pro Asn Asp Ser Lys Arg Val Gln Lys His Pro Ala Thr Phe Gln
            530                 535                 540

Cys His Leu Cys Pro Lys Arg Phe Thr Arg Ala Tyr Asn Leu Arg Ser
545                 550                 555                 560
```

```
His Leu Arg Thr His Thr Asp Glu Arg Pro Phe Val Cys Thr Val Cys
                565                 570                 575
Gly Lys Ala Phe Ala Arg Gln His Asp Arg Lys Arg His Glu Gly Leu
            580                 585                 590
His Ser Gly Glu Lys Lys Phe Val Cys Arg Gly Asp Leu Ser Arg Gly
        595                 600                 605
Gly Gln Trp Gly Cys Gly Arg Arg Phe Ala Arg Ala Asp Ala Leu Gly
    610                 615                 620
Arg His Phe Arg Ser Glu Ala Gly Arg Ile Cys Ile Lys Pro Leu Leu
625                 630                 635                 640
Asp Glu Glu Ser Gln Glu Arg Glu Arg Thr Leu Met Asp Gln Gln Asn
                645                 650                 655
Gln Gln His Ala Gly His Leu Gln Pro Val Pro Gln Pro Leu Met Val
            660                 665                 670
Pro Gly Met Asp Gly Gln His Ala Asn Gly Phe Val Leu Pro Ala Ala
        675                 680                 685
Leu Leu Ala Gln Tyr Pro Ala Leu Gln Asn Leu Gln Trp Asp Gln Ile
    690                 695                 700
Thr Ala Ala Ala Glu Asp Pro Ser Asp Ile Gly Gly Arg Ser Ser Phe
705                 710                 715                 720
Asp Ala Ser Ser Gly Gly Glu Phe Gly Phe Glu Asp Asp Glu Ser Asn
                725                 730                 735
Leu Ser Ser Val Ser Gly Met Ser Gly Tyr Gly Ser Pro Gln Asp Asn
            740                 745                 750
Leu Tyr Val Met Asn Asn Gln Asn Gln Met Leu Asn Val Asn Pro Gly
        755                 760                 765
Asp Ser Gly Tyr Ala
    770

<210> SEQ ID NO 7
<211> LENGTH: 31
<212> TYPE: DNA
<213> ORGANISM: Artificial Sequence
<220> FEATURE:
<223> OTHER INFORMATION: synthetic primer

<400> SEQUENCE: 7
ggcctctaga tccacccggc tgcacatcac c                              31

<210> SEQ ID NO 8
<211> LENGTH: 32
<212> TYPE: DNA
<213> ORGANISM: Artificial Sequence
<220> FEATURE:
<223> OTHER INFORMATION: synthetic primer

<400> SEQUENCE: 8
cccctccgga cagcactggg acccgactca ac                             32

<210> SEQ ID NO 9
<211> LENGTH: 24
<212> TYPE: DNA
<213> ORGANISM: Artificial Sequence
<220> FEATURE:
<223> OTHER INFORMATION: synthetic primer

<400> SEQUENCE: 9
tgtgaaggcg ctacgcaaga acga                                      24
```

```
<210> SEQ ID NO 10
<211> LENGTH: 29
<212> TYPE: DNA
<213> ORGANISM: Artificial Sequence
<220> FEATURE:
<223> OTHER INFORMATION: synthetic primer

<400> SEQUENCE: 10
ttcctgacaa cgaggacatc tcaagctgt                                           29

<210> SEQ ID NO 11
<211> LENGTH: 24
<212> TYPE: DNA
<213> ORGANISM: Artificial Sequence
<220> FEATURE:
<223> OTHER INFORMATION: synthetic primer

<400> SEQUENCE: 11
cagaggggcg ctgagctgag gtaa                                                24

<210> SEQ ID NO 12
<211> LENGTH: 36
<212> TYPE: DNA
<213> ORGANISM: Artificial Sequence
<220> FEATURE:
<223> OTHER INFORMATION: synthetic primer

<400> SEQUENCE: 12
ggtcagtaac atagcaggac tatagtagtg gctcac                                   36

<210> SEQ ID NO 13
<211> LENGTH: 2548
<212> TYPE: DNA
<213> ORGANISM: Trichoderma reesei

<400> SEQUENCE: 13
gaaacgcagc tcagactgtg attcgcaccg ctgtacgcgt cctgccgctg tgatagggcc         60
gcaccccccc agcaccttgc attgctgccg ccagtgcaca gcctcctcgg aaggctgact        120
gtggaatctg cctcgcgaca acgaggtacg gagacagaca gaccaagcgc tcggccgcca        180
tcatggccca tgaacccccag cgtggaaggt cgccgtcggc cggtggcttt cagtctgata      240
taaaccaatc ccactcgccg gcacggagcc cgctggcacc cacaaatgag cagccatccg        300
ctggtcttgg agttggactc ggcgtcgacc tggattcgtc acagcagcaa caacaactgc        360
agcagcagca gcaacagcaa caacaacagc gactccagca gcagcaacaa cgagcattcg        420
cggcgcctct gcatcccaac tacgactcct ttggcgcaaa cggcttcctc ggcgcacaag        480
ccaacgccgt cgacccgaca aacggctttg atcccagcgc gagcttcgga cagcagccgg        540
ccaccggccc cgactccacc ctctccctga cgcccaggc gcaacacaac tacctctccc         600
caaacctcca cgacggtgac ttctctctct ttccctcagc cgctgagcaa ggcgatcagt        660
acaacgcccc cctcttcgag cagccgcctc tgggcgacct caatgccatg acctccccgc        720
actcgcatca gtctccgacc cctccacagc tcttccagcc ggacagtcta cagtcgcctc        780
ccttcaaccg acatcagttc tcgtcgccgc caactcattc gagaaatgct tccctaggac        840
ccgaagccgc gcttctccct agccagattg gagactggac ccagccgcag tttcagggtc        900
atcgacgaac ccctctgag tattcggacg tctcctccgt ggccccttcg ccccatctcg         960
tcagttccga tacgttcgac gccgaccagt cgggccactc gcctctgcag aggcccgcgg       1020
atgttagcct ctaccaggaa gtgctcggca tcggatcctt cagcctggct gaccacggta       1080
```

-continued

```
gtcccgggta tcatggtcga agtccctcgc acagtccagc catcagccct cggataatgc      1140
cccagcagat gccggacacc atgcagccct ctttcaacct cattccgccc aatggcggct      1200
ttgacggagt atcaggatac ccggacctgc aacctagcca tgagagcttt ccctcgctat      1260
caggcggcat gggcggcgat atgcaccaga tggcgccccc agccatcaac atcgactttg      1320
cgccgaccaa ttcgagacag ggcagctttg agccgcccaa gtcgcagatg gatcaagatt      1380
cgctaacacc accagaaaga ggtaggtcct cattcacttt gcaacatggg tctaccaact      1440
gtaggcgcct aactgacgcg ggtattacag gtcgtccaaa atctcgcccg agagcggtca      1500
cggacccgtt ccaccccggt agcggaatac tgcccccctgg caatctgggc tcctctctcg     1560
gcgttgatct tgcggcccgt tccgacacag catctcgatc cttatcccct ctagacaggt      1620
caggaaccag ctcaccagca tctcgaaggc gacaatcgac ttcttcggtg ccgaacaacg      1680
tcatagcgtt acgcctggcg gacccggagt atcagaacag ccaagaagcc ggcacaagca      1740
agcgcatgca gaagcacccg gcgaccttc agtgtaccttt gtgtcccaag agattcacca      1800
gagcttataa cttgcgctct cacctgcgaa ctcataccga tgagcgtccc ttcgtgtgca      1860
ctgtctgcgg taaagcattt gctcgacagc atgacaggaa acggcacgaa agtttgcact      1920
caggagagaa gaagtttgtc tgtaagggg atctcaaaac tggtggacaa tggggatgcg      1980
gccgacggtt tgcgcgagcg gacgccttgg gaagacattt ccggtccgaa gcaggcagga      2040
tatgcatcaa gcccctccta gatgaagaaa tggtcgaaag gcaacgccag tggcaggaac      2100
agcggatgca gcagaatatg gcgcaaaaca tggccaaccc gcaggtcatg ggcatggatg      2160
ccggcccagc ttatcctatg gacgccagcg gaaattacac tctcccgcaa gctctcctgg      2220
ctcaatatcc agcactggcg cagatgaact ggtcagcgac agatatggga ggcgggctgg      2280
acgatgagct cagcggaagg tcgtcatttg acgccagtga ctacgatgac ggtgacgacg      2340
gtggctacat cagtagttct ggggccagat atccagaaga aggcatgagt cagaattatg      2400
ccgacatgaa ttatatggga gactacgggc gctgaggagg ctctcatgaa ttctttacat      2460
cttctttctc ttccacacct agctgtcttc tttcccgacc ctctacccca gccccatttt      2520
tcgacttgct tgtatccaac cctttcct                                         2548
```

FILAMENTOUS FUNGI HAVING AN ALTERED VISCOSITY PHENOTYPE

CROSS REFERENCE TO RELATED APPLICATIONS

The present application is a 371 National Stage application of PCT/US2012/034405, filed on Apr. 20, 2012, which claims priority to U.S. Provisional Application Ser. Nos. 61/478,162, and 61/478,160, both filed on Apr. 22, 2011 and 61/480,610, 61/480,602 and 61/480,629, each filed on Apr. 29, 2011, which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40011WO_ST25.txt" created on Oct. 11, 2013, which is 40,056 bytes in size.

TECHNICAL FIELD

The present strains and methods relate to genetic mutations in filamentous fungi that give rise to strain variants having altered growth characteristics. Such variants are well-suited for growth in submerged cultures, e.g., for the large-scale production of enzymes and other proteins or metabolites for commercial applications.

BACKGROUND

Filamentous fungi are capable of expressing native and heterologous proteins to high levels, making them well-suited for the large-scale production of enzymes and other proteins for industrial, pharmaceutical, animal health and food and beverage applications. Filamentous fungi are typically grown in mycelial submerged cultures in bioreactors, which are adapted to introduce and distribute oxygen and nutrients into the culture medium (i.e., broth). The morphological characteristics of the mycelium affect the rheological properties of the broth, thereby affecting bioreactor performance.

Generally, the higher the viscosity of the broth, the less uniform the distribution of oxygen and nutrients, and the more energy required to agitate the culture. In some cases, the viscosity of the broth becomes sufficiently high to significantly interfere with the dissolution of oxygen and nutrients, thereby adversely affecting the growth of the fungi. Additionally, the power required to mix and aerate viscous broth can significantly increase the cost of production, and incur higher capital expenditures in terms of motors and power supplies.

SUMMARY

Described are strains and methods relating to filamentous fungi having genetic alterations that give rise to altered viscosity phenotypes.

In one aspect, a variant strain of filamentous fungus derived from a parental strain is provided, the variant strain comprising a genetic alteration that causes cells of the variant strain to produce an altered amount of functional Crz1 protein compared to cells of the parental strain, wherein the cells of the variant strain are produced during aerobic fermentation in submerged culture cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

In some embodiments, the altered amount of functional Crz1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

In some embodiments, the genetic alteration comprises a disruption of the crz1 gene present in the parental strain. In some embodiments, disruption of the crz1 gene is the result of deletion of all or part of the crz1 gene. In some embodiments, disruption of the crz1 gene is the result of deletion of a portion of genomic DNA comprising the crz1 gene. In some embodiments, disruption of the crz1 gene is the result of mutagenesis of the crz1 gene.

In some embodiments, disruption of the crz1 gene is performed using site-specific recombination. In some embodiments, disruption of the crz1 gene is performed in combination with introducing a selectable marker at the genetic locus of the crz1 gene.

In some embodiments, the variant strain does not produce functional Crz1 protein. In some embodiments, the variant strain does not produce Crz1 protein.

In some embodiments, the variant strain further comprises a gene encoding a protein of interest. In some embodiments, the variant strain further comprises a disruption of the sfb3 gene. In some embodiments, the variant strain further comprises a disruption of the seb1 gene. In some embodiments, the variant strain further comprises a disruption of the sfb3 and seb1 genes. In some embodiments, the variant strain further comprises a disruption of at least one gene selected from the group consisting of the sfb3 gene, the seb1 gene, the mpg1 gene, the gas1 gene, and the tps2 gene. In some embodiments, the variant strain produces substantially the same amount of, or more, protein per unit amount of biomass as the parental strain.

In some embodiments, the filamentous fungus is a Pezizomycotina species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum,* and *Chrysosporium lucknowense*. In some embodiments, the filamentous fungus is *Trichoderma reesei*.

In another aspect, a method for producing a variant strain of filamentous fungus cells is provided, comprising: introducing a genetic alteration into a parental strain of filamentous fungal cell, which genetic alteration alters the production of functional Crz1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the genetic alteration reduces or prevents the production of functional Crz1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

In some embodiments, the genetic alteration comprises disrupting the crz1 gene in a parental filamentous fungal cell using genetic manipulation. In some embodiments, the genetic alteration comprises deleting the crz1 gene in a parental filamentous fungal cell using genetic manipulation. In some embodiments, the genetic alteration is performed using site-specific genetic recombination.

In some embodiments, disruption of the crz1 gene is performed in combination with introducing a selectable marker at the genetic locus of the crz1 gene. In some embodiments, the variant strain produces substantially the same amount of, or more, protein per unit amount of biomass as the parental strain. In some embodiments, disruption of the crz1 gene is performed in combination with disrupting the sfb3 gene. In some embodiments, disruption of the crz1 gene is performed in combination with disrupting at least one gene selected from the group consisting of the sfb3 gene, the seb1 gene, the mpg1 gene, the gas1 gene, and the tps2 gene.

In some embodiments, the variant strain produces substantially the same amount of, or more, protein per unit amount of biomass as the parental strain.

In some embodiments, the filamentous fungus is a Pezizomycotina species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*. In some embodiments, the filamentous fungus is *Trichoderma reesei*.

In some embodiments, the parental strain further comprises a gene encoding a protein of interest. In some embodiments, the gene encoding the protein of interest is present in the parental strain prior to introducing the genetic alteration that reduces or prevents the production of functional Crz1 protein. In some embodiments the protein of interest within the parental strain is encoded by an endogenous gene or a heterologous gene.

In another aspect, a protein of interest produced by any of the aforementioned variant strains is provided.

In yet another aspect, a filamentous fungus produced by any of the aforementioned methods and having any of the aforementioned properties is provided.

In another aspect, a variant strain of filamentous fungus derived from a parental strain is provided, the variant strain comprising: (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and (b) a gene encoding a protein of interest, wherein the gene encoding the protein of interest is present in the variant strain prior to the genetic alteration in (a).

In some embodiments, the genetic alteration of the resulting variant strain comprises a disruption of the crz1 gene present in the parental strain. In some embodiments, disruption of the crz1 gene is performed in combination with introducing a selectable marker at the genetic locus of the crz1 gene. In some embodiments, disruption of the crz1 gene is performed in combination with disrupting the sfb3 gene. In some embodiments, disruption of the crz1 gene is performed in combination with disrupting the seb1 gene. In some embodiments, disruption of the crz1 gene is performed in combination with disrupting at least one gene selected from the group consisting of the sfb3 gene, the seb1 gene, the mpg1 gene, the gas1 gene, and the tps2 gene.

These and other aspects and embodiments of present variant strains and methods will be apparent from the description, including the accompanying FIGURE.

BRIEF DESCRIPTION OF THE DRAWING

FIG. 1 is a map of the crz1 disruption vector, pRATT261-crz1D, as described in Example 1.

DETAILED DESCRIPTION

I. Overview

The present strains and methods relate to variant strains of filamentous fungus cells having genetic modifications that affect their morphology and growth characteristics. When the variant cells are grown in submerged culture, they produce a cell broth that has different rheological properties compared to a cell broth comprising cells of the parental strain. Some of these variant strains are well-suited for the large-scale production of enzymes and other commercially important proteins.

II. Definitions

Prior to describing the present strains and methods in detail, the following terms are defined for clarity. Terms not defined should be accorded their ordinary meanings as used in the relevant art.

As used herein, "*Trichoderma reesei*" refers to a filamentous fungus of the phylum Ascomycota, subphylum Pezizomycotina. This organism was previously classified as *Trichoderma longibrachiatum*, or as *Hypocrea jecorina*.

As used herein, the phrase "variant strain of filamentous fungus cells," or similar phrases, refer to strains of filamentous fungus cells that are derived (i.e., obtained from or obtainable from) from a parental (or reference) strain belonging to the Pezizomycotina, e.g., by genetic manipulation. In the present description, parental and variant strains can be described as having certain characteristics, such as genetic modifications, expression phenotypes, morphology, and the like; however, the skilled person will appreciate that it is technically the cells of the parental or variant strain that have such characteristics, and "the strains" are referred to for convenience.

As used herein, the term "protein of interest" refers to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are deemed "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "derivative polypeptide/protein" refers to a protein, which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence, which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. Homologs are not necessarily evolutionarily related. Thus, it is intended that the term encompasses the same, similar, or corresponding enzyme(s) (e.g., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989)

*Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (e.g., wild-type) sequence. Sequence identity can be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases can be searched using FASTA (Pearson et al. (1988) *Proc. Natl. Acad. Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, or strains found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a function gene product, e.g., a protein, in a host cell. Examples of methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression.

As used herein, the terms "genetic manipulation" and "genetic alteration" are used interchangeably and refer to the alteration/change of a nucleic acid sequence. The alteration can included but is not limited to a substitution, deletion, insertion or chemical modification of at least one nucleic acid in the nucleic acid sequence.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, the term "rheology" refers to a branch of physics dealing with the deformation and flow of matter.

As used herein, "viscosity" is a measure of the resistance of a fluid to deformation by mechanical stress, such as shear stress or tensile stress. In the present context, viscosity can also refer to the resistance of a cell broth comprising filamentous fungus cells to mechanical stress, e.g., as provided by a rotor/impeller. Because the viscosity of a cell broth can be difficult to measure directly, indirect measurements of viscosity can be used, such as the dissolved oxygen content of the culture broth at a preselected amount of agitation, the amount of agitation required to maintain a preselected dissolved oxygen content, the amount of power required to agitate a cell broth to maintain a preselected dissolved oxygen content, or even colony morphology on solid medium.

As used herein, an "altered-viscosity" variant strain of filamentous fungus cells refers to a variant strain that produces a cell broth that has a reduced or increased viscosity (i.e., reduced or increased resistance to shear or tensile stress) compared to an equivalent cell broth produced by a parental strain. Generally, comparable cell broths or equivalent cell broths have comparable cell masses. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cells broth are described herein.

As used herein, a "reduced-viscosity" variant strain of filamentous fungus cells refers to a variant strain that produces a cell broth that has reduced viscosity (i.e., reduced resistance to shear or tensile stress) compared to an equivalent cell broth produced by a parental strain. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more.

As used herein, "dissolved oxygen" (DO) refers to the amount of oxygen ($O_2$) present in a liquid medium as measured in vol/vol units. The dissolved oxygen level can be maintained at a high level, e.g., between 170-100% and 20%, between 100-80% and 20%, between 70% and 20%, between 65% and 20%, between 60% and 20%, between 55% and 20%, between 50% and 20%, between 45% and 20%, between 44% and 20%, between 43% and 20%, between 42% and 20%, between 41% and 20%, between 40% and 20%, between 35% and 20%, between 30% and 20%, and between 25% and 20% throughout the fermentation. In particular, the dissolved oxygen can be high at the beginning of the fermentation and to be permitted to fall as the fermentation progresses. The dissolved oxygen level can be controlled by the rate at which the fermentation is agitated, e.g. stirred, and/or by the rate of addition of air or oxygen. The culture can be agitated, e.g., stirred at between 400-700 rpm and the dissolved oxygen level is maintained above 20%, above 25%, above 30%, above 35%, above 40%, above 45%, above 50% and above 55% or more by altering the air or oxygen flow rate and impeller speed.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, variant cells "maintain or retain a high level of protein expression and/or secretion" compared to a parental strain if the difference in protein expression between the variant strain and a parental strain is less than about 20%, less than about 15%, less than about 10%, less than about 7%, less than about 5%, or even less than about 3%.

As used herein, host cells have been "modified to prevent the production of a specified protein" if they have been genetically or chemically altered to prevent the production of a functional protein/polypeptide that exhibits an activity characteristic of the wild-type protein, particularly an activity that promotes elongation of hyphae or otherwise increases the viscosity of a filamentous fungus in liquid culture. Such modifications include, but are not limited to, deletion or disruption of the gene encoding the protein, modification of the gene such that the encoded polypeptide lacks the aforementioned activity, modification of the gene to affect post-translational processing or stability, and combinations, thereof.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

As used herein, a variant strain produces "substantially the same amount" of protein per unit amount of biomass as a parental strain if the amount of protein produced by the variant strain is no more than 20% reduced, no more than 15% reduced, no more than 10% reduced, an even no more than 5% reduced compared to the amount of protein produced by the parental strain, wherein the amount of protein is normalized to the total amount of biomass of cells from which protein production is measured, wherein biomass can be expressed in terms of either wet (e.g., of cell pellet) or dry weight.

As used herein, a variant strain produces "substantially more protein per unit amount of biomass" than a parental strain if the amount of protein produced by the variant strain is at least 5% increased, at least 10% increased, at least 15% increased, or more, compared to the parental strain, wherein the amount of protein is normalized to the total amount of biomass of cells from which protein production is measured, wherein biomass can be expressed in terms of either wet (e.g., of cell pellet) or dry weight.

As used herein, "fluorochromes" are fluorescent dyes. Preferred fluorochromes bind to cellulose and/or chitin in the cell walls of fungi.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

CFU colony forming units
EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
DO dissolved oxygen
g or gm gram
µg microgram
mg milligram
kg kilogram
lb pound
µL and µl microliter
mL and ml milliliter
mm millimeter
µm micrometer
mol mole
mmol millimole
M molar
mM millimolar
µM micromolar
nm nanometer
U unit
ppm parts per million
sec and " second
min and ' minute
hr and h hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute
Δ relating to a deletion
CER $CO_2$ evolution rate
bp base pairs

III. Filamentous Fungal Strain with Altered Crz1 Protein Production

In one aspect, a variant strain of filamentous fungus derived from a parental strain is provided, the variant strain comprising a genetic alteration that causes cells of the variant strain to produce an altered amount of functional Crz1 protein compared to cells of the parental strain. The cells of the variant strain subsequently produce, during aerobic fermentation in submerged culture, a cell broth that requires an altered amount of agitation to maintain a preselected dissolved oxygen content, or a cell mass that maintains an altered dissolved oxygen content at a preselected amount of agitation, compared to the cells of the parental strain.

In some cases, the genetic alteration causes cells of the variant strain to produce a reduced amount of functional Crz1 protein compared to cells of the parental strain, and the resulting cell broth requires reduced agitation to maintain a preselected dissolved oxygen content, or maintains a higher dissolved oxygen content at a preselected amount of agitation, compared to the cells of the parental strain. In such cases, it is believed that the cell mass of the variant strain exhibits reduced viscosity compared to the cell mass of the parental strain, which accounts for the observations relating to dissolved oxygen content and agitation as described in the Examples.

The reduction in the amount of functional Crz1 protein can result from disruption of the crz1 gene present in the parental strain. Because disruption of the crz1 gene is a primary genetic determinant for conferring a reduced viscosity phenotype to the variant strain, such variant strains need only comprise a disrupted crz1 gene, while all other genes can remain intact. In some cases, the variant strains can optionally include additional genetic alterations compared to the parental stain from which they are derived. Such additional genetic alterations are not necessary to confer a reduction in viscosity but can further reduce viscosity or confer other advantages for the variant strain.

Disruption of the crz1 gene can be performed using any suitable methods that substantially prevent expression of a function crz1 gene product, i.e., the Crz1 protein. Exemplary methods of disruption as are known to one of skill in the art include but are not limited to: Complete or partial deletion of the crz1 gene, including complete or partial deletion of, e.g., the Crz1-coding sequence, the promoter, the terminator, an enhancer, or another regulatory element; and complete or partial deletion of a portion of the chromosome that includes any portion of the crz1 gene. Particular methods of disrupting the crz1 gene include making nucleotide substitutions or insertions in any portion of the crz1 gene, e.g., the Crz1-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can be used to disrupt the crz1 gene.

Mutations in the crz1 gene can reduce the efficiency of the crz1 promoter, reduce the efficiency of a crz1 enhancer, interfere with the splicing or editing of the crz1 mRNA, interfere with the translation of the crz1 mRNA, introduce a stop codon into the Crz1-coding sequence to prevent the translation of full-length Crz1 protein, change the coding sequence of the Crz1 protein to produce a less active or inactive protein or reduce Crz1 interaction with other nuclear protein components, change the coding sequence of the Crz1 protein to produce a less stable protein or target the protein for destruction, cause the Crz1 protein to misfold or be incorrectly modified (e.g., by glycosylation), or interfere with cellular trafficking of the Crz1 protein.

In one embodiment, these and other genetic manipulations is to reduce or prevent the expression of a functional Crz1 protein, or reduce or prevent the normal biological activity of the Crz1 protein, thereby producing a morphology change that results in a reduced viscosity phenotype.

In other cases, the genetic alteration increases or restores the expression of a functional Crz1 protein, or increases the normal biological activity of the Crz1 protein, thereby producing a morphology change that results in an increased or restored viscosity phenotype. Exemplary genetic alterations that increase or restore Crz1 function are those that introduce addition copies of the crz1 gene into a cell, increase the efficiency of the crz1 promoter, enhancer, or other control element, increase the translation of the mRNA encoding the Crz1 protein, increase the stability of mRNA encoding the Crz1 protein, introduce changes in the crz1 gene that increase the activity or stability of the Crz1 protein, introduce changes in the crz1 gene that modulate the interaction with other proteins or nucleic acids and the like. Other genetic alterations that increase or restore Crz1 function are those that reverse the effect of genetic alterations, which reduce or prevent the expression of a functional Crz1 protein.

Filamentous fungus cells for manipulation and use as described are generally from the phylum Ascomycota, subphylum Pezizomycotina, particularly fungi that have a vegetative hyphae state and include a homolog of the crz1 gene. Such organisms include filamentous fungus cells used for the production of commercially important industrial and pharmaceutical proteins, including, but are not limited to *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. Particular organisms include, but are not limited to, *Trichoderma reesei* (previously classified as *Trichoderma longibrachiatum* or *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum,* and *Chrysosporium lucknowense.*

In fungi, calcineurin mediated $Ca^{2+}$ signaling has been shown to be required for growth, development, and virulence in many organisms. It is necessary for adaption to diverse environmental conditions including high cation levels and alkaline pH. The gene crz1 encodes a calcineurin-regulated transcription factor. The Crz1p transcription factor is dephosphorylated when the phosphatase calcineurin is activated by $Ca^{2+}$/calmodulin. It then enters the nucleus and induces expression of a number of genes, many of which encode proteins with cell wall-related functions (Yoshimoto et al., 2002; Lagorce et al., 2003; Garcia et al., 2004; Karababa et al., 2006; Pardini et al., 2006, Munro, C. et al. 2009). Deletion of crz1 or a homolog can result in alterations in hyphal morphology (Kothe, G. and Free, S. 1998, Prokisch, H. et al. 1997). The present disclosure provides experimental evidence of the association of Crz1 with altered morphology.

Not wishing to be bound to a theory, it is believed that the alteration of crz1 expression and/or activity in filamentous fungi can alter the cell wall, thereby producing a more compact cellular morphology characterized by shorter hyphae and a more yeast-like appearance.

Using BLAST to search publicly available genome sequences of filamentous fungi and yeast using the *T. reesei* Crz1 amino acid sequence as query, homologs were found, although the function of these proteins was heretofore unknown. The amino acid sequences of the *T. reesei* (SEQ ID NO:1), *E. nidulans* (SEQ ID NO:2), *S. cerevisiae* (SEQ ID NO:3), *A. fumigatus* (SEQ ID NO:4), *P. marneffei* (SEQ ID NO:5), and *A. flavus* (SEQ ID NO:6) Crz1 proteins are shown below.

The predicted amino acid sequence of the *T. reesei* Crz1 protein is shown below as SEQ ID NO:1:

RGRSPSAGGFQSDINQSHSPARSPLAPTNEQPSAGLGVGLGQQQQRAFAA

PLHPNYDSFGANGFLGAQANAVDPTNGFDPSASFGQQPATGPDSTLSLNA

QAQHNYLSPNLHDGDFSLFPSAAEQGDQYNAPLFEQPPLGDLNAMTSPHS

HQSPTPPQLFQPDSLQSPPFNRHQFSSPPTHSRNASLGPEAALLPSQIGD

WTQPQFQGHRRTPSEYSDVSSVAPSPHLVSSDTFDADQSGHSPLQRPADV

SLYQEVLGIGSFSLADHGSPGYHGRSPSHSPAISPRIMPQQMPDTMQPSF

NLIPPNGGFDGVSGYPDLQPSHESFPSLSGGMGGDMHQMAPPAINIDFAP

TNSRQGSFEPPKSQMDQDSLTPPERGRPKSRPRAVTDPFHPGSGILPPGN

LGSSLGVDLAARSDTASRSLSPLDRSGTSSPASRRRQSTSSVPNNVIALR

LADPEYQNSQEAGTSKRMQKHPATFQCTLCPKRFTRAYNLRSHLRTHTDE

RPFVCTVCGKAFARQHDRKRHESLHSGEKKFVCKGDLKTGGQWGCGRRFA

RADALGRHFRSEAGRICIKPLLDEEMVERQRQWQEQRMQQNMAQNMANPQ

VMGMDAGPAYPMDASGNYTLPQALLAQYPALAQMNWSATDMGGGLDDELS

GRSSFDASDYDDGDDGGY

The amino acid sequence of the *Emericella nidulans* Crz1 protein is shown below as SEQ ID NO: 2:

MDPQDTLQDLGQAPAAHINRSASPSAHAHQQYNNNHNDLTIDPSVTSNSS

YPPSSFANNSAPGSEAFAYSSSYLTPATATDHNFARPSLQIPQSFDQGLS

HQPAEENFSNLLNSNTGDFDFSLYQGSSPNNTGSDYPSSGLLDPQQSGNQ

AVNPVDLVSQIPSPHPSNSSQTSPLDQPPSSAMSPPASSPGTFYTPQHSR

HTSLDPASAAYMTNVSHPEWQAVMNNSAFHGHRRAPSEVSEVSSAAHSPY

LPQHDSFDVADNNPSPLLAAQNDPSLYDNAALGIESFTLSEHHQPQTQGI

SPHHSPYISPQLMPQHPTDIIPGGPFISAPATNSAYPTPPTEGYPNGGDI

GQASQMAPPSINVEFAPPAKAQVFPPEKSTADMDSLSPPPSLRTSRMRSK

SDPYAVSISRPRSPSSPSASLDALAASSPRSLSPFNVGRHPYSNPSSREP

SPARSARRLSTSSVDSRNYILGLADPQRPGSNNTDSKRVQKHPATFQCTL

CPKRFTRAYNLRSHLRTHTDERPFVCTVCGKAFARQHDRKRHEGLHSGEK

KFVCRGDLSRGGQWGCGRRFARADALGRHFRSEAGRICIKPLLDEESQER

ERTLINQQQQHLQPVNQPLMLPGQGTEAQHTGSFILPAALLAQYPALQTL

QWDQIPAGTDDTSDIGGRNSFDASSGGEFGFDDDESGISVSGMSTGYASD

QGNIYNVDAQGQMLGVNPGEAGYANPNWGK

The amino acid sequence of the *Saccharomyces cerevisiae* Crz1 protein is shown, below, as SEQ ID NO: 3:

MSFSNGNMASYMTSSNGEEQSINNKNDIDDNSAYRRNNFRNSSNSGSHTF

QLSDLDLDVDMRMDSANSSEKISKNLSSGIPDSFDSNVNSLLSPSSGSYS

ADLNYQSLYKPDLPQQQLQQQQLQQQQQQQQQQQQQQQKQTPTLKVEQSD

TFQWDDILTPADNQHRPSLTNQFLSPRSNYDGTTRSSGIDSNYSDTESNY

HTPYLYPQDLVSSPAMSHLTANNDDFDDLLSVASMNSNYLLPVNSHGYKH

ISNLDELDDLLSLTYSDNNLLSASNNSDFNNSMNGIINTADTQNSTIAIN

KSKVGTNQKMLLTIPTSSTPSPSTHAAPVTPIISIQEFNEGHFPVKNEDD

GTLQLKVRDNESYSATNNNNLLRPDDNDYNNEALSDIDRSFEDIINGRKL

KLKKSRRRSSQTSNNSFTSRRSSRSRSISPDEKAKSISANREKLLEMADL

LPSSENDNNRERYDNDSKTSYNTINSSNFNEDNNNNNLLTSKPKIESGIV

NIKNELDDTSKDLGILLDIDSLGQFEQKVGFKNDDNHENNDNGTFSVKKN

DNLEKLDSVTNNRKNPANFACDVCGKKFTRPYNLKSHLRTHTNERPFICS

ICGKAFARQHDRKRHEDLHTGKKRYVCGGKLKDGKPWGCGKKFARSDALG

RHFKTESGRRCITPLYEEARQEKSGQES

The amino acid sequence of the *Aspergillus fumigatus* Crz1 protein is shown below as SEQ ID NO:4:

MASQEMFPELGQSPAPGVKSRGVSRSPHPHQQQQQQQHQQHQGQFTGTVT

GLDLDSSIATASSFANSSFDPNSNNVSPSAESYGYTAAGYLSGTPASQTD

QNYANSLQIPQSYGTGLVPQFNESRGLPIQQQSQQQHHQQPSLDDNFSDL

LNSNATEYDFNTVYQTHSPSSNTAPEYDSSLLLDPQVHQQSHPTQIPSSH

SSTSPQISPLEQQQHSSPGPMSTQGSTTVAYYTPQHSRHASLDPATAAFL

TSNTHPDWQAVMGNSAAFQGHRRAPSEVSEISSAAPSPYLSQHESFDGVD

NNPSPLLAPQNDPSLYDSALGIENFTLSEQHQQHQGFSPAHSPYISPRLM

PQQGQEMMPNVPYLSGPAPNTQYPTPPNDMYGNGAEGMMNMSQGTHPSVD

IGQASQMAPPSINVEFAPPSRIPSFGPSKPASNLDSLSPPPSSTRSRGRS

KSDPYAHPSTSRLRSSSTSSSLDPLAPTTPRSLSPFDSFGRQQQSNPSSR

DPSPSRSNRRLSTSSIDSRNYILGLADPQRPGASPNDSKRVQKHPATFQC

NLCPKRFTRAYNLRSHLRTHTDERPFVCTVCGKAFARQHDRKRHEGLHSG

EKKFVCQGELSRGGQWGCGRRFARADALGRHFRSEAGRICIKPLLDEESQ

ERERSLMDQQQHHLQPLPQQVMVPVDNPHAGNFVLPAALLAQYPALQTLQ

WDQIAASADDPSDIGGRSSFDASSGNEFGFEDDDSGLSSVSGINAGYSAA

GNFY

The amino acid sequence of the *Penicillium marneffei* Crz1 protein is shown below as SEQ ID NO:5:

MENHGQYANRGRSPSASVHSRNVSPSPHHGQHSPYHDPSAAGLMLDASTA

GTGYQSNLTFTTAPPLSSSLAPDSNNPDLYNNFLTATTTSQQHDSLAAQN

DQFASSVAATFQDQLDQSATHQDANYSNLLNPNPNDYDFTQYAVGGDNAV

MQSAFDSSLLLDQQQQQQQQQQQHNTQNVQLMGQGDMTQMGSPNNLLSPE

-continued

HHSSPGNSHTSPPISSGPFYSPGHSRSASLDPMSAAYMSNHNQAQDWKNM

LENHSFQSHRRAPSEHSDVSSVAHSPYAGHHESFDALDGASPSLGAQNDP

VLYDNTLAMDSFTLSEQQQGLSPHHSPYISPQMPSQDITSDAFILSGQQN

MTQFPTLPHDIFTGQPDDGMLAGTQAPDMSGLDANQMNNMVPPPSINVEF

APPSRMPSFGPGGENDFDALSPPSRGSRGRSKSDPFGRPTPIVRPHSQSV

SSTSSLDPAVGSSPRSLSPFDSMGGSRSNPGSRGVSPASRSSIRRQSTSS

IERKVILDLADPQRPGATPGESKRTQKHPATFQCNLCPKRFTRAYNLRSH

LRTHTDERPFVCTVCGKAFARQHDRKRHEGLHSGEKKFVCRGDLASRGQW

GCGRRFARADALGRHFRSEAGRACIKALLDEEAIERNRIFMEQQAQQQAQ

QQHLQPVPQPLMVPGLDNQAGFTLPAALLAQYPALQNLQWDQIATSGTDD

VSDISARNSFDAGSGGEFGFDDDDLSIGSFTGASGQGVIYAGGSHPTSAP

NFALEATDPNFTGQEWSQ

The amino acid sequence of the *Aspergillus flavus* Crz1 protein is shown below as SEQ ID NO:6:

MASQDTLRDAGQSTADVKNRSVSPSAHPQHQYNNASPGLTLDPSFTVSSF

QNSASFNANPNSNSPGADSYSYTAGGYLSPTSAQTLAPPDQAFSHSLQLQ

SFDPGLVNQLDHSSGLSMQPQLQQHQQPHEENFSTLLNSNPTDFDFSLYP

NHSPNSTTASEYDSSLMLDTQMQGHPQQVNQAVNPVDLIGQMPSPHSVTS

PQMSPQEQQPHHSSPGPMSPPNSTPGAYYTPQHSRHTSLDPASAAYMTGN

APPDWQSMMGNAAFQGHRRAPSEVSEVSSAAPSPYMSHHESFDGVDNNPS

PLLAPQNDPGLYDSSLGIESFTLSEQQQQQQHQQGISPIHSPYISPQLMP

QQGNDLIPNMPYISAPAGNRYSCPPTDIYGNGAEGVISMPQGTAMVGDIG

QASQMAPPSINVEFAPPAKNPIFPPAKPAADLDSLSPPPSTRRMRSKSDP

YAHPASRSRSPVSVSSSLEPLAPSSPRSLSPFDSTGRQPHSNPSSREPSP

SRSRRLSTSSIDNRNYILGLADPQRPGASPNDSKRVQKHPATFQCHLCPK

RFTRAYNLRSHLRTHTDERPFVCTVCGKAFARQHDRKRHEGLHSGEKKFV

CRGDLSRGGQWGCGRRFARADALGRHFRSEAGRICIKPLLDEESQERERT

LMDQQNQQHAGHLQPVPQPLMVPGMDGQHANGFVLPAALLAQYPALQNLQ

WDQITAAAEDPSDIGGRSSFDASSGGEFGFEDDESNLSSVSGMSGYGSPQ

DNLYVMNNQNQMLNVNPGDSGYA

In some embodiments of the present compositions and methods, the amino acid sequence of the Crz1 protein that is altered in production levels has a specified degree of overall amino acid sequence identity to the amino acid sequence of SEQ ID NOs: 1, 2, 3, 4, 5, or 6, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, 5, or 6. The nucleotide sequences encoding each amino acid sequence can be identified from a BLAST search for each corresponding protein as is know to one skilled in the art.

In some embodiments of the present compositions and methods, the crz1 gene that is disrupted encodes a Crz1 protein that has a specified degree of overall amino acid sequence identity to the amino acid sequence of SEQ ID NOs: 1, 2, 3, 4, 5, or 6, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, 5, or 6.

The amino acid sequence information provided herein readily allows the skilled person to identify a Crz1 protein, and the nucleic acid sequence encoding a Crz1 protein, in any filamentous fungi, and to make appropriate disruptions in the crz1 gene to affect the production of the Crz1 protein. The polynucleotide sequences encoding SEQ ID NOs: 1, 2, 3, 4, 5, and 6 can be found in the GenBank or JGI databases, as are known to one of skill in the art.

In another aspect, a method for altering the morphology of filamentous fungus cells is provided. The variant filamentous fungus cells exhibit altered growth morphology on solid medium and produce cell broth having different viscosities when grown in submerged culture compared to parental cell growth and cell broth viscosities.

In some cases, the method comprises disrupting the crz1 gene in a parental strain using suitable genetic methods, wherein during aerobic fermentation the disrupted crz1 variant strain produces during aerobic fermentation in submerged culture a cell broth that requires reduced agitation to maintain a preselected dissolved oxygen content, or maintains an increased dissolved oxygen content at a preselected amount of agitation, compared to the cells of the parental strain. Such methods can be used to disrupt the crz1 gene in any manner described above and elsewhere as are known to one of skill in the art. Preferably, disruption of the crz1 gene is performed by genetic manipulation using sequence-specific molecular biology techniques, as opposed to chemical mutagenesis, which is generally not targeted to specific nucleic acid sequences. However, chemical mutagenesis can also be used to achieve satisfactory results.

In some embodiments, the parental strain into which the reduced viscosity phenotype is introduced creating a reduced viscosity strain already comprises a gene of interest intended to be expressed at high levels. In this manner, the present methods obviate the need to introduce a gene of interest into a pre-existing reduced viscosity strain for production. Thus, the present methods can be used to produce a reduced viscosity variant strain of filamentous fungus cells from a parental strain already comprising a gene of interest.

VI. Utility

The use of reduced viscosity strains of filamentous fungi is known to improve the distribution of oxygen and nutrients in a submerged culture, reduce the amount of energy required to agitate a submerged culture, and increase the cell mass present in the culture, leading to increased protein production. Moreover, the present variant strains of filamentous fungus offer significant advantages over previously-described reduced viscosity strains.

First, the present strains can have a fully defined genome, making them well-suited for subsequent genetic manipulation, complementation, mating, and the like. Second, the present strains are still capable of high levels of protein production, for example, by the manipulation(s) that resulted in the attendant viscosity alteration. Third, reduced viscosity strains can be produced from essentially any parental strain, including parental strains that already produce a protein intended for high level expression (i.e., a protein of interest), already encoding a selectable marker, or already including other features that are desirable in a production host. Thus, the present strain and methods eliminate the need to transfer a gene encoding a protein of interest into a preexisting reduced viscosity production strain.

The present strains and methods find use in the production of commercially important protein in submerged cultures of filamentous fungi. Commercially important proteins include, for example, cellulases, xylanases, pectinases, lyases, proteases, kinases, amylases, pullulanases, lipases, esterases, perhydrolases, transferases, laccases, catalases, oxidases, reductases, chlorophyllases, hydrophobin, chymosin, carbonic anhydrase, hymidylate synthase, dihydrofolate reductase, tyrosine kinases, multi-drug resistance proteins (e.g., ABC P-gp proteins), CAD (carbamyl-P synthase, aspartate transcarbamylase, dihydroorotase), topoisomerases, ribonucleotide reductase, and antibodies and other enzymes and non-enzyme proteins capable of being expressed in filamentous fungi. Such proteins can be suitable for industrial, pharmaceutical, animal health and food and beverage use.

The following numbered paragraphs further describe various aspects and embodiments of the present compositions and methods. The subject matter of each of the numbered paragraphs can be used alone or in combination with the subject matter of any other numbered paragraph, as indicated.

1. In one aspect, a variant strain of filamentous fungus derived from a parental strain is provided, the variant strain comprising a genetic alteration that causes cells of the variant strain to produce an altered amount of functional Crz1 protein compared to cells of the parental strain, wherein the cells of the variant strain produce during aerobic fermentation in submerged culture a cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

2. In some embodiments of the variant strain of paragraph 1, the altered amount of functional Crz1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

3. In some embodiments of the variant strain of paragraphs 1 or 2, the genetic alteration comprises a disruption of the crz1 gene present in the parental strain.

4. In some embodiments of the variant strain of paragraph 3, disruption of the crz1 gene is the result of deletion of all or part of the crz1 gene.

5. In some embodiments of the variant strain of paragraph 3, disruption of the crz1 gene is the result of deletion of a portion of genomic DNA comprising the crz1 gene.

6. In some embodiments of the variant strain of any claim 3, disruption of the crz1 gene is the result of mutagenesis of the crz1 gene.

7. In some embodiments of the variant strain of any of paragraphs 3-6, disruption of the crz1 gene is performed using site-specific recombination.

8. In some embodiments of the variant strain of any of paragraphs 3-7, disruption of the crz1 gene is performed in combination with introducing a selectable marker at the genetic locus of the crz1 gene.

9. In some embodiments of the variant strain of any of paragraphs 1-8, the variant strain does not produce functional Crz1 protein.

10. In some embodiments of the variant strain of any of paragraphs 1-8, the variant strain does not produce Crz1 protein.

11. In some embodiments of the variant strain of any of paragraphs 1-10, the variant strain further comprises a gene encoding a protein of interest.

12. In some embodiments of the variant strain of any of paragraphs 1-11, further comprising a disruption of the sfb3 gene.

13. In some embodiments of the variant strain of any of paragraphs 1-12, further comprising a disruption of at least one gene selected from the group consisting of the sfb3 gene, the seb1 gene, the mpg1 gene, the gas1 gene, and the tps2.

14. In some embodiments of the variant strain of any of paragraphs 1-13, the variant strain produces substantially the same amount of, or more, protein per unit amount of biomass as the parental strain.

15. In some embodiments of the variant strain of any of paragraphs 1-14, the filamentous fungus is a Pezizomycotina species.

16. In some embodiments of the variant strain of any of paragraphs 1-15, the filamentous fungus is a *Trichoderma* spp.

17. In some embodiments of the variant strain of any of paragraphs 1-16, the filamentous fungus is *Trichoderma reesei*.

18. In another aspect, a method for producing a variant strain of filamentous fungus cells is provided, comprising: introducing a genetic alteration into a parental strain of filamentous fungal cell, which genetic alteration alters the production of functional Crz1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

19. In some embodiments of the method of paragraph 18, the genetic alteration reduces or prevents the production of functional Crz1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

20. In some embodiments of the method of paragraph 18 or 19, the genetic alteration comprises disrupting the crz1 gene in a parental filamentous fungal cell using genetic manipulation.

21. In some embodiments of the method of any of paragraphs 18-20, the genetic alteration comprises deleting the crz1 gene in a parental filamentous fungal cell using genetic manipulation.

22. In some embodiments of the method of any of paragraphs 18-21, the genetic alteration is performed using site-specific genetic recombination.

23. In some embodiments of the method of any of paragraphs 18-22, disruption of the crz1 gene is performed in combination with introducing a selectable marker at the genetic locus of the crz1 gene.

24. In some embodiments of the method of any of paragraphs 18-23, disruption of the crz1 gene is performed in combination with disrupting the sfb3 gene.

25. In some embodiments of the method of any of paragraphs 18-24, disruption of the crz1 gene is performed in combination with disruption of at least one gene selected from the group consisting of the sfb3 gene, the seb1 gene, the mpg1 gene, the gas1 gene, and the tps2 gene.

26. In some embodiments of the method of any of paragraphs 18-25, the variant strain produces substantially the same amount of, or more, protein per unit amount of biomass as the parental strain.

27. In some embodiments of the method of any of paragraphs 18-26, the filamentous fungus is a Pezizomycotina species.

28. In some embodiments of the method of any of paragraphs 18-27, the filamentous fungus is a *Trichoderma* spp.

29. In some embodiments of the method of any of paragraphs 18-28, the filamentous fungus is *Trichoderma reesei*.

30. In some embodiments of the method of any of paragraphs 18-29, the parental strain further comprises a gene encoding a protein of interest.

31. In some embodiments of the method of paragraph 30, the gene encoding the protein of interest is present in the parental strain prior to introducing the genetic alteration that reduces or prevents the production of functional Crz1 protein.

32. In another aspect, a protein of interest produced by the variant strain of paragraph 11 is provided.

33. In another aspect, a variant strain of filamentous fungus produced by the method of any of paragraphs 18-31 is provided.

34. In another aspect, a variant strain of filamentous fungus derived from a parental strain is provided, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
(b) a gene encoding a protein of interest, wherein the gene encoding the protein of interest is present in the variant strain prior to the genetic alteration in (a).

35. In some embodiments of the variant strain of paragraph 34, the genetic alteration comprises a disruption of the crz1 gene present in the parental strain.

36. In some embodiments of the variant strain of paragraph 35, disruption of the crz1 gene is performed in combination with introducing a selectable marker at the genetic locus of the crz1 gene.

37. In some embodiments of the variant strain of paragraph 35 or 36, disruption of the crz1 gene is performed in combination with disrupting at least one gene selected from the group consisting of the sfb3 gene, the seb1 gene, the mpg1 gene, the gas1 gene, and the tps2 gene.

38. In some embodiments of the variant strain of any of paragraphs 35-37, disruption of the crz1 gene is performed in combination with disrupting the seb1 gene.

These and other aspects and embodiments of the present strains and methods will be apparent to the skilled person in view of the present description. The following examples are intended to further illustrate, but not limit, the strains and methods.

EXAMPLES

Example 1. Deletion of the Crz1 Gene from *T. reesei* Mutant Morph 77B7

A *Trichoderma reesei* Morph strain was deleted for four major cellulase genes, including cbhI, cbhII, egII, and egIV, which makes it particular suitable for expressing other proteins in the absence of or in reduced cellulase background. See, WO 05/001036.

A. TrGA Producing Strain Morph 77B7

The Morph strain, described above, was previously transformed with a native *Trichoderma* glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoro-orotic acid (FOA) selection.

B. Generation of a Crz1 Disruption Cassette

The *Trichoderma reesei* crz1 (PID 36391) was deleted from mutant Morph 77B7.

The crz1 disruption cassette plasmid pRATT261 (FIG. 1) was prepared using standard molecular biology procedures. This plasmid included a DNA sequence having a 2.6 Kb region homologous to the DNA sequence spanning part of the third exon and contiguous upstream sequences (Left Flank). Also included within the plasmid was a DNA sequence having a 2.4 Kb region homologous to the DNA sequence spanning part of the third exon of the crz1 gene and contiguous downstream sequences (Right Flank). These sequences were designed to target the crz1 gene and replace the regions of the genome between the Left and Right Flanks, region 122703 to 123270 on Scaffold 4, with the intervening cassette sequences. These intervening sequences included a pyr2 selection marker from *Trichoderma atroviride* intended to minimize homology to the endogenous *T. reesei* pyr2 in the genome of the strain to be transformed. Immediately upstream of the pyr2 selection marker was a directly repeated duplication of the 3' end of the marker, which facilitated the subsequent loss of the marker and isolation of useful pyr2 mutant derivatives of the transformants/disruptants. This crz1 disruption cassette was amplified by PCR using primers RPG486 and RPG489. Multiple PCR reactions were pooled and cleaned using standard molecular biology procedures for use in the subsequent steps.

The nucleic acid sequence of the crz1 gene was obtained from the JGI data base: Protein ID: 36391, Name: gw1.4.693.1, available at genome.jgi.psf.org, (The Genome Portal of the Department of Energy Joint Genome Institute I. V. Grigoriev, H. Nordberg, I. Shabalov, A. Aerts, M. Cantor, D. Goodstein, A. Kuo, S. Minovitsky, R. Nikitin, R. A. Ohm, R. Otillar, A. Poliakov, I. Ratnere, R. Riley, T. Smirnova, D. Rokhsar, and I. Dubchak. Nucleic Acids Res 2011 0: gkr947v1-gkr947) as disclosed below. The untranslated region is italicized and flanked 5' and 3' by upstream or downstream sequence, coding regions are in bold and introns are in lower case (SEQ ID NO: 13):

GAAACGCAGCTCAGACTGTGATTCGCACCGCTGTACGCGTCCTGCCGCTG

TGATAGGGCCGCACCCCCCCAGCACCTTGCATTGCTGCCGCCAGTGCACA

GCCTCCTCGGAAGGCTGACTGTGGAATCTGCCTCGCGACAACGAGGTACG

-continued
```
GAGACAGACAGACCAAGCGCTCGGCCGCCATCATGGCCCATGAACCCCAG

CGTGGAAGGTCGCCGTCGGCCGGTGGCTTTCAGTCTGATATAAACCAATC

CCACTCGCCGGCACGGAGCCCGCTGGCACCCACAAATGAGCAGCCATCCG

CTGGTCTTGGAGTTGGACTCGGCgtcgacctggattcgtcacagcagcaa caacaactgcagcagcagcagcaacagcaacaacaacagcgactccagCA

GCAGCAACAACGAGCATTCGCGGCGCCTCTGCATCCCAACTACGACTCCT

TTGGCGCAAACGGCTTCCTCGGCGCACAAGCCAACGCCGTCGACCCGACA

AACGGCTTTGATCCAGCGCGAGCTTCGGACAGCAGCCGGCCACCGGCCC

CGACTCCACCCTCTCCTGAACGCCCAGGCGCAACACAACTACCTCTCCC

CAAACCTCCACGACGGTGACTTCTCTCTCTTTCCCTCAGCCGCTGAGCAA

GGCGATCAGTACAACGCCCCCCTCTTCGAGCAGCCGCCTCTGGGCGACCT

CAATGCCATGACCTCCCCGCACTCGCATCAGTCTCCGACCCCTCCACAGC

TCTTCCAGCCGGACAGTCTACAGTCGCCTCCCTTCAACCGACATCAGTTC

TCGTCGCCGCCAACTCATTCGAGAAATGCTTCCCTAGGACCCGAAGCCGC

GCTTCTCCCTAGCCAGATTGGAGACTGGACCCAGCCGCAGTTTCAGGGTC

ATCGACGAACCCCTCTGAGTATTCGGACGTCTCCTCCGTGGCCCCTTCG

CCCCATCTCGTCAGTTCCGATACGTTCGACGCCGACCAGTCGGGCCACTC

GCCTCTGCAGAGGCCCGCGGATGTTAGCCTCTACCAGGAAGTGCTCGGCA

TCGGATCCTTCAGCCTGGCTGACCACGGTAGTCCCGGGTATCATGGTCGA

AGTCCCTCGCACAGTCCAGCCATCAGCCCTCGGATAATGCCCCAGCAGAT

GCCGGACACCATGCAGCCCTCTTTCAACCTCATTCCGCCCAATGGCGGCT

TTGACGGAGTATCAGGATACCCGGACCTGCAACCTAGCCATGAGAGCTTT

CCCTCGCTATCAGGCGGCATGGGCGGCGATATGCACCAGATGGCGCCCCC

AGCCATCAACATCGACTTTGCGCCGACCAATTCGAGACAGGGCAGCTTTG

AGCCGCCCAAGTCGCAGATGGATCAAGATTCGCTAACACCACCAGAAAGA

Ggtaggtcctcattcactttgcaacatgggtctaccaactgtaggcgcct aactgacgcgggtattacagGTCGTCCAAAATCTCGCCCGAGAGCGGTCA

CGGACCCGTTCCACCCCGGTAGCGGAATACTGCCCCCTGGCAATCTGGGC

TCCTCTCTCGGCGTTGATCTTGCGGCCCGTTCCGACACAGCATCTCGATC

CTTATCCCCTCTAGACAGGTCAGGAACCAGCTCACCAGCATCTCGAAGGC

GACAATCGACTTCTTCGGTGCCGAACAACGTCATAGCGTTACGCCTGGCG

GACCCGGAGTATCAGAACAGCCAAGAAGCCGGCACAAGCAAGCGCATGCA

GAAGCACCCGGCGACCTTTCAGTGTACCTTGTGTCCCAAGAGATTCACCA

GAGCTTATAACTTGCGCTCTCACCTGCGAACTCATACCGATGAGCGTCCC

TTCGTGTGCACTGTCTGCGGTAAAGCATTTGCTCGACAGCATGACAGGAA

ACGGCACGAAAGTTTGCACTCAGGAGAGAAGAAGTTTGTCTGTAAGGGGG

ATCTCAAAACTGGTGGACAATGGGGATGCGGCCGACGGTTTGCGCGAGCG

GACGCCTTGGGAAGACATTTCCGGTCCGAAGCAGGCAGGATATGCATCAA

GCCCCTCCTAGATGAAGAAATGGTCGAAAGGCAACGCCAGTGGCAGGAAC

AGCGGATGCAGCAGAATATGGCGCAAAACATGGCCAACCCGCAGGTCATG

GGCATGGATGCCGGCCCAGCTTATCCTATGGACGCCAGCGGAAATTACAC

TCTCCCGCAAGCTCTCCTGGCTCAATATCCAGCACTGGCGCAGATGAACT

GGTCAGCGACAGATATGGGAGGCGGGCTGGACGATGAGCTCAGCGGAAGG

TCGTCATTTGACGCCAGTGACTACGATGACGGTGACGACGGTGGCTACAT

CAGTAGTTCTGGGGCCAGATATCCAGAAGAAGGCATGAGTCAGAATTATG

CCGACATGAATTATATGGGAGACTACGGGCGCTGAGGAGGCTCTCATGAA

TTCTTTACATCTTCTTTCTCTTCCACACCTAGCTGTCTTCTTTCCCGACC

CTCTACCCCAGCCCCATTTTTCGACTTGCTTGTATCCAACCCTTTCCT
```

C. Generation of Strain Morph 77B7 Δcrz1

Strain Morph TrGA 77B7 Δpyr2 was transformed with the crz1 disruption cassette using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the crz1 disruption cassette integrated at the crz1 locus by homologous recombination. Homologous integration of the Δcrz1 disruption cassette at the crz1 locus was verified by amplifying DNA fragments of the expected sizes using two primer pairs. Primer pair RPG492 and RPG253 amplified a DNA fragment starting outside the 5' end of the disruption cassette region and ending within 3' region. Primer pair RPG491 and RPG273 amplified a DNA fragment starting within the 5' region of the disruption cassette and ending outside the 3' end of the disruption cassette region. The generated strain with confirmed homologous integration of the crz1 disruption cassette was named Morph 77B7 Δcrz1.

TABLE 1

Primers used in example 1

| Primer | Sequence | SEQ ID NO |
|---|---|---|
| RPG486 | 5'-GGCCTCTAGATCCACCCGGCTGCACATCACC-3' | 7 |
| RPG489 | 5'-CCCCTCCGGACAGCACTGGGACCCGACTCAAC-3' | 8 |
| RPG492 | 5'-TGTGAAGGCGCTACGCAAGAACGA-3' | 9 |
| RPG253 | 5'-TTCCTGACAACGAGGACATCTCAAGCTGT-3' | 10 |
| RPG491 | 5'-CAGAGGGGCGCTGAGCTGAGGTAA-3' | 11 |
| RPG273 | 5'-GGTCAGTAACATAGCAGGACTATAGTAGTGGCTCAC-3' | 12 |

Morph 77B7 Δcrz1 obtained from the above procedure was observed to have altered morphology in liquid culture having shorter filaments than the Morph 77B7 parent. In liquid medium, cultures containing the Morph 77B7 Δcrz1 mutant also showed a higher level of dissolved oxygen during growth compared to cultures containing the Morph 77B7 parent (Table 2).

Strains Morph 77B7 and Morph 77B7 Δcrz1 were grown under similar conditions in submerged (liquid) culture, and their growth phenotypes were compared. Briefly, spores of each strain were added separately to 500-mL of minimal medium in a 3-L flask with both side and bottom baffles. After autoclaving for 30 minutes, sterile 60% glucose was added to a final concentration of 27.5 g/L. The cultures were grown for 48 hrs at 34° C. in a shaking incubator.

After 48 hrs, the contents of each flask were added separately to 14-L fermentors containing 9.5 L of medium containing 4.7 g/L KH$_2$PO$_4$, 1.0 g/L MgSO$_4$.7H$_2$O, 4.3 g/L (NH$_4$)$_2$SO$_4$ and 2.5 mL/L of the same trace element solution. These components were heat sterilized together at 121° C. for 30 min. A solution of 60% glucose and 0.48% CaCl$_2$.2H$_2$O was separately autoclaved, cooled, and added to the fermentor to a final concentration of 75 g/L glucose and 0.6 g/L CaCl$_2$.2H$_2$O. The medium was adjusted to pH 3.5 with 28% NH$_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO content levels dropped, at least partly as a consequence of the increased viscosity of the broth due to the proliferation of filamentous fungus hyphae. When DO content level fell below 40%, the agitation rate was increased to maintain the DO content level at 40%. Upon reaching 750 rpm agitation, the DO content level would be allowed to drop below 40%. If the DO content level did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for both strains.

The DO content level in each fermentor at a given level of agitation, and the amount of agitation required to maintain a given DO content level are indirect measures of the viscosity of the different broths, due to the different strain growth phenotypes. Although it would be ideal to vary only one variable (e.g., DO content or agitation) and measure the other, it is desirable to prevent the DO content level from falling below 40% to ensure the production of sufficient biomass in each fermentor, thereby permitting a more meaningful comparison among the growth characteristics of the different strains.

Generally, where it is necessary to increase the agitation rate to maintain a target DO content level, the amount of agitation can be estimated by the amount of power supplied to the motor driving the fermentor turbine, which provides a metric that correlates with the viscosity of the broth. In particular, the extra power required to agitate the suspended culture is proportional to the agitation rate raised to the 3rd power.

As shown in Table 2, Morph 77B7 Δcrz1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δcrz1 did not require as much energy to achieve the same biomass concentration. Agitation rate never increased above 500 rpm and the % DO never dropped below 100.

TABLE 2

Broth viscosity of Morph 77B7 compared to Morph 77b7 Δcrz1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δcrz1 | crz1 | 100 | 500 | 39 | 120 |

Example 2. Additive Effect Produced by Altering at Least One of Sfb3, Seb1, Mpg1, Gas1, and Tps2 Production A. Viscosity Reduction in Disrupted Sbf3

The Sfb3 gene (also known as Lst1) has previously only been characterized in budding yeast (i.e., *Saccharomyces cerevisiae*), where it encodes a protein associated with the COPII protein coat surrounding transport vesicles that carry proteins from the endoplasmic reticulum to the Golgi apparatus. Sfb3, as well as Sfb2, are homologs of Sec24, all of which genes are involved with packaging specific cargo proteins into the vesicles.

As shown in Table 3, disrupting the sfb3 gene from strain 29-9 Δsfb3 resulted in a strain having a reduction in the highest agitation rate required to maintain the dissolved oxygen at 40% at the end of the growth phase. Under these growth conditions, the original strain, 29-9, required 2.6 times more power than either the 70H2 (chemically mutagenized 29-9) or 29-9 Δsfb3 strains in order to maintain a DO of 40% and produce the amount of biomass. Strains 70H2 and 29-9 Δsfb3 had similar viscosity properties, and produced similar levels of a protein of interest (TrGA) in suspended culture, demonstrating that a reduced viscosity growth phenotype can be imparted to a filamentous fungus by disrupting the sfb3 gene. Alterations in the Sfb3 protein resulting in alterations in viscosity are further described in PCT Publication No. WO 2012/027580 A1, published 1, Mar. 2012, filed as International Application No. PCT/US2011/049164, filed 25, Aug. 2011, incorporated herein by reference.

TABLE 3

Agitation rate required to maintain a DO of 40% at the end of the growth phase

| Strain | Agitation rate | Relative power increase from baseline at 500 rpm |
|---|---|---|
| 29-9 | 750 | $(750/500)^3 = 3.4$ |
| 70H2 | 539 | $(539/500)^3 = 1.3$ |
| 29-9 Δsfb3 | 540 | $(540/500)^3 = 1.3$ |

B. Viscosity Reduction in Disrupted Seb1

Seb1 from *Trichoderma atroviride* is a STRE-element-binding protein, and the seb1 gene is believed to be an orthologue of the yeast msn2/4 gene and the *Aspergillus nidulans* msnA gene. Notably, the seb1 gene cannot complement the msn2/4 gene in yeast, so is probably not a functional homologue (Peterbauer, C. et al. ((2002) *Molecular Genetics and Genomics* 268:223-31). Seb1 is involved with but not essential in the osmotic stress response but has been found to be associated with altered morphology, particularly those giving rise to a low viscosity phenotype when seb1 is disrupted. Details of the seb1 disruption can be found in U.S. Provisional Application No. 61/478,160, filed Apr. 22, 2011, incorporated by reference herein in its entirety.

As shown in Table 4, deletion of the seb1 gene from strain Morph1/1 Δku80 resulted in a strain having a reduction in broth viscosity. At the end of the batch growth phase, when all the glucose has been consumed, both strains had achieved a similar biomass concentration. To get there, the control strain saw agitation increased to the maximum of 750 rpm and then saw DO drop down to as low as 29%. The seb1 deleted strain did not require as much energy to achieve the same biomass concentration. Agitation rate was never increased above 500 rpm and DO dropped only as low as 55%.

TABLE 4

Broth viscosity in Morph1/1 Δku80 with and without the seb1 gene

| Strain | Dele-tion | DO (%) | Agitation (rpm) | Biomass (g/kg) | CER (mmol/L/hr) |
|---|---|---|---|---|---|
| Morph1.1Δku80 | none | 29 | 750 | 38 | 157 |
| Morph1.1Δku80, Δpyr4, Δseb1 | seb1 | 55 | 500 | 37 | 138 |

C. Viscosity Reduction in Disrupted Mpg1

The mpg1 gene encodes a GTP:alpha-D-mannose-1-phoshate guanyltransferase. Over-expression of the mpg1 gene increases GDP-mannose levels, which can play a major regulatory role in early stages of protein glycosylation.

As shown in Table 5, MAGI 10-8 g, the mpg1 deletion variant strain, has a reduction in broth viscosity compared to the parent MAGI. At the end of the batch growth phase, when all the glucose has been consumed, both strains had achieved a similar biomass concentration. To get there, the MAGI control strain saw agitation increased to the maximum of 750 rpm and then saw DO drop down to as low as 35%. The strain MAGI 10-8 g did not require as much energy to achieve the same biomass concentration. Agitation rate was increased slightly to 513 rpm when the % DO dropped to 40%. Protein production was not adversely affected in MAGI 10-8 g compared to MAGI (not shown). Details of the mpg1 disruption can be found in U.S. Provisional Application No. 61/478,162, filed Apr. 22, 2011, incorporated by reference herein in its entirety.

TABLE 5

Broth viscosity of MAGI compared to MAGI 10-8 g

| Strain | Dele-tion | DO (%) | Agitation (rpm) | Biomass (g/kg) | CER (mmol/L/hr) |
|---|---|---|---|---|---|
| MAGI | none | 35 | 750 | 39 | 125 |
| MAGI 10-8 g | mpg1 | 40 | 513 | 40 | 128 |

D. Viscosity Reduction in Disrupted Gas1

The Gel/Gas/Phr family of fungal β(1,3)-glucanosyltransferases plays an important role in cell wall biogenesis by processing the main component β(1,3)-glucan (Popolo et al., 2008). gas1 (PID 22914) encodes a beta-1,3-glucanosyltransferase that is a GPI (and/or glucan)-anchored protein capable of breaking and joining beta-1,3-glucans. There are multiple paralogs in many fungal genomes including *T. reesei*, which has five. Separate studies have shown that mutation of the gas1 gene (or the gel1 gene as it is known in *Aspergillus fumigatus*) affects fungal cell wall structure, and can lead to morphological changes as well as hypersensitivity to Calcofluor White, Congo Red and sodium dodecyl sulfate (Schirawski et al., The Plant Cell, Vol. 17: 3532-3543, 2005; Mouyna et al., Molecular Microbiology, 56(6): 1675-1688, 2005).

A *Trichoderma reesei* Morph strain was deleted for four major cellulase genes, including cbhI, cbhII, egII, and egIV, which makes it particular suitable for expressing other proteins in the absence of or in reduced cellulase background. See, WO 05/001036. The Morph strain had been previously transformed with a native *Trichoderma* glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoroorotic acid (FOA) selection. The *Trichoderma reesei* gas1 (PID 22914) was deleted from mutant Morph 77B7.

Strain Morph TrGA 77B7 Δpyr2 was transformed with a gas1 disruption cassette using PEG-mediated transformation, and plated on Vogel's minimal medium containing sorbitol to select for candidates based on uridine prototrophy acquired by the pyr2 marker. As shown in Table 6, Morph 77B7 Δgas1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δgas1 did not require as much energy (i.e., rpm increase in agitation) to achieve the same biomass concentration. Agitation rate never increased above 500 rpm and the % DO never dropped below 115. Protein production was not adversely affected in Morph 77B7 Δgas1 compared to Morph 77B7 (data not shown). Details of the gas1 disruption can be found in U.S. Provisional Application No. 61/480, 602, filed Apr. 29, 2011, incorporated by reference herein in its entirety.

TABLE 6

Broth viscosity of Morph 77B7 compared to Morph 77b7 Δgas1

| Strain | Dele-tion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δgas1 | gas1 | 115 | 500 | 39 | 147 |

E. Viscosity Reduction in Disrupted Tps1

The gene tps2 encodes a trehalose-phosphate phosphatase involved in the synthesis of the disaccharide trehalose. Trehalose is a stress induced sugar that buffers the refolding of denatured proteins in the cytoplasm and ER (Singer, M et al. 1998, Simola, M et al. 2000). This disaccharide is produced in large quantities by diverse organisms in response to a variety of stresses. In yeast, trehalose stabilizes proteins at high temperatures and assists in refolding heat damaged proteins (Simola, M et al. 2000).

A *Trichoderma reesei* Morph strain was prepared as described above. The *Trichoderma reesei* tps2 (PID 48707) was deleted from mutant Morph 77B7. Strain Morph TrGA 77B7 Δpyr2 was transformed with the tps2 disruption cassette using PEG-mediated transformation, and plated on Vogel's minimal medium containing sorbitol to select for candidates based on uridine prototrophy acquired by the pyr2 marker. As shown in Table 7, Morph 77B7 Δtps2 has a reduction in broth viscosity compared to the parent Morph 77B7. At the end of the batch growth phase, when all the glucose had been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δtps2 did not require as much energy to achieve the same biomass concentration. Agitation rate never increased above 500 rpm and the % DO never dropped below 110. Details of the tps1 disruption can be found in U.S. Provisional Application No. 61,480,629, filed Apr. 29, 2011, incorporated by reference herein in its entirety.

TABLE 7

Broth viscosity of Morph 77B7 compared to Morph 77b7 Δtps2

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δtps2 | tps2 | 110 | 500 | 41 | 94 |

Although the foregoing compositions and methods have been described in some detail by way of illustration and examples for purposes of clarity of understanding, it will be apparent to those skilled in the art that certain changes and modifications can be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

REFERENCES

The following references, and additional reference cited herein, are hereby incorporated by reference:

Kothe, G. and Free, S. (1998) *Fungal Genet. Biol* 23:248-258.
Prokisch, H., et al. (1997) *Gen. Genet.* 256:104-114.
Yoshimoto et al. (2002) *J. Biol. Chem.* 227:31079-31088.
Lagorce et al. (2003) *J. Biol. Chem.* 278:20345-20357.
Garcia et al. (2004) *J. Biol. Chem.* 279:15183-15195.
Karababa et al. (2006) *Mol. Microbiol.* 59:1429-1451.
Pardini et al. (2006) *J. Biol. Chem.* 281:40399-40411.
Munro, C. et al. (2009) *Mol. Microbiol.* 63:1399-1413.
Hughes, H. and Stephens, D. J. (2008) *Cell. Biol.* 129:129-51.
Karhinen, L. et al. (2005) *Traffic* 6:562-74.
Passolunghi, S. et al. (2010) *Microbial Cell Factories* 9:7-17.
Peng, R. et al. (2000) *J. Biol. Chem.* 275:11521-28.
Roberg, K. J. et al. (1999) *J. Cell. Biol.* 145:659-72.
Shimoni, Y. et al. (2000) *J. Cell. Biol.* 151:973-84.
Turchini, A. et al. (2000) *J. Bacteriol.* 182:1167-71.

What is claimed is:

1. A variant strain of filamentous fungus derived from a parental strain, the variant strain comprising a genetic alteration that causes cells of the variant strain to produce a reduced amount of functional Crz1 protein compared to cells of the parental strain, wherein the cells of the variant strain during aerobic fermentation in submerged culture (i) require a reduced amount of agitation to maintain a preselected dissolved oxygen content compared to the cells of the parental strain, and/or (ii) maintain an increased dissolved oxygen content at a preselected amount of agitation, compared to the cells of the parental strain.

2. The variant strain of claim 1, wherein the genetic alteration comprises a disruption of the crz1 gene present in the parental strain.

3. The variant strain of claim 2, wherein disruption of the crz1 gene is the result of deletion of all or part of the crz1 gene.

4. The variant strain of claim 2, wherein disruption of the crz1 gene is the result of deletion of a portion of genomic DNA comprising the crz1 gene.

5. The variant strain of claim 2, wherein disruption of the crz1 gene is the result of mutagenesis of the crz1 gene.

6. The variant strain of claim 2, wherein disruption of the crz1 gene is performed using site-specific recombination.

7. The variant strain of claim 2, wherein disruption of the crz1 gene is performed in combination with introducing a selectable marker at the genetic locus of the crz1 gene.

8. The variant strain of claim 1, wherein the variant strain does not produce functional Crz1 protein.

9. The variant strain of claim 1, wherein the variant strain does not produce Crz1 protein.

10. The variant strain of claim 1, wherein the variant strain further comprises a gene encoding a heterologous protein of interest.

11. The variant strain of claim 1, further comprising a disruption of the sfb3 gene.

12. The variant strain of claim 1, further comprising a disruption of at least one gene selected from the group consisting of the sfb3 gene, the seb1 gene, the mpg1 gene, the gas1 gene, and the tps2 gene.

13. The variant strain of claim 1, wherein the variant strain produces substantially the same amount of, or more, protein per unit amount of biomass as the parental strain.

14. The variant strain of claim 1, wherein the filamentous fungus is a Pezizomycotina species.

15. The variant strain of claim 1, wherein the filamentous fungus is a *Trichoderma* spp.

16. The variant strain of claim 1, wherein the filamentous fungus is *Trichoderma reesei*.

17. A method for producing a variant strain of filamentous fungus cells comprising: introducing a genetic alteration into a parental strain of filamentous fungal cell, which genetic alteration reduces the production of functional Crz1 protein compared to the cells of the parental strain, thereby producing a variant filamentous fungal cell that during aerobic fermentation in submerged culture (i) requires a reduced amount of agitation to maintain a preselected dissolved oxygen content, compared to the cells of the parental strain, and/or (ii) maintains an increased dissolved oxygen content at a preselected amount of agitation, compared to the cells of the parental strain.

18. The method of claim 17, wherein the genetic alteration comprises disrupting the crz1 gene in the parental filamentous fungal cell using genetic manipulation.

19. The method of claim 17, wherein the genetic alteration comprises deleting the crz1 gene in a parental filamentous fungal cell using genetic manipulation.

20. The method of claim 17, wherein the genetic alteration is performed using site-specific genetic recombination.

21. The method of claim 17, wherein disruption of the crz1 gene is performed in combination with introducing a selectable marker at the genetic locus of the crz1 gene.

22. The method of claim 17, wherein disruption of the crz1 gene is performed in combination with disrupting the sfb3 gene.

23. The method of claim 17, wherein disruption of the crz1 gene is performed in combination with disruption of at least one gene selected from the group consisting of the sfb3 gene, the seb1 gene, the mpg1 gene, the gas1 gene, and the tps2 gene.

24. The method of claim 17, wherein the variant strain produces substantially the same amount of, or more, protein per unit amount of biomass as the parental strain.

25. The method of claim 17, wherein the filamentous fungus is a Pezizomycotina species.

26. The method of claim 17, wherein the filamentous fungus is a *Trichoderma* spp.

27. The method of claim 17, wherein the filamentous fungus is *Trichoderma reesei*.

28. The method of claim 17, wherein the parental strain further comprises a gene encoding a heterologous protein of interest.

29. The method of claim 28, wherein the gene encoding the protein of interest is present in the parental strain prior to introducing the genetic alteration that reduces or prevents the production of functional Crz1 protein.

30. A variant strain of filamentous fungus derived from a parental strain, the variant strain comprising:
    (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
    (b) a gene encoding a heterologous or an endogenous protein of interest,
    wherein the gene encoding the protein of interest is present in the variant strain prior to the genetic alteration in (a).

31. The variant strain of claim 30, wherein the genetic alteration comprises a disruption of the crz1 gene present in the parental strain.

32. The variant strain of claim 31, wherein disruption of the crz1 gene is performed in combination with introducing a selectable marker at the genetic locus of the crz1 gene.

33. The variant strain of claim 32, wherein disruption of the crz1 gene is performed in combination with disrupting at least one gene selected from the group consisting of the sfb3 gene, the seb1 gene, the mpg1 gene, the gas1 gene, and the tps2 gene.

34. The variant strain of claim 33, wherein disruption of the crz1 gene is performed in combination with disrupting the seb1 gene.

35. The variant strain of claim 1, wherein the variant strain comprises a gene encoding an endogenous protein of interest.

36. The method of claim 17, wherein the parental strain comprises a gene encoding an endogenous protein of interest.

* * * * *